(12) United States Patent
Robinson et al.

(10) Patent No.: US 11,357,258 B2
(45) Date of Patent: Jun. 14, 2022

(54) CARTRIDGE FOR HAVING A SLEEVE WITH SLOTS SURROUNDING A CONTACT PIECE WITH CORRESPONDING CONTACT ARMS

(71) Applicant: BRITISH AMERICAN TOBACCO (INVESTMENTS) LIMITED, London (GB)

(72) Inventors: Joe Robinson, London (GB); Joseph Sutton, London (GB)

(73) Assignee: Nicoventures Trading Limited, London (GB)

( * ) Notice: Subject to any disclaimer, the term of this patent is extended or adjusted under 35 U.S.C. 154(b) by 0 days.

(21) Appl. No.: 15/540,731

(22) PCT Filed: Dec. 18, 2015

(86) PCT No.: PCT/EP2015/080595
§ 371 (c)(1),
(2) Date: Jun. 29, 2017

(87) PCT Pub. No.: WO2016/107768
PCT Pub. Date: Jul. 7, 2016

(65) Prior Publication Data
US 2018/0042302 A1  Feb. 15, 2018

(30) Foreign Application Priority Data
Dec. 29, 2014  (GB) .................................. 1423318

(51) Int. Cl.
*A24F 40/42* (2020.01)
*A61M 15/06* (2006.01)
*A24F 40/20* (2020.01)

(52) U.S. Cl.
CPC ............. *A24F 40/42* (2020.01); *A61M 15/06* (2013.01); *A24F 40/20* (2020.01)

(58) Field of Classification Search
CPC ...... A24F 47/008; A24F 47/002; A24F 40/00; A24F 40/46; A24F 40/20; A24F 40/42; A24F 40/44; A61M 15/06
(Continued)

(56) References Cited

U.S. PATENT DOCUMENTS

| 4,735,217 A | 4/1988 | Gerth et al. |
| 4,947,874 A | 8/1990 | Brooks et al. |

(Continued)

FOREIGN PATENT DOCUMENTS

| AT | 507 187 | 3/2010 |
| AU | 2015373527 B2 | 5/2019 |

(Continued)

OTHER PUBLICATIONS

Application and File History for U.S. Appl. No. 15/540,704, filed Jun. 29, 2017, inventors Singh.

(Continued)

*Primary Examiner* — Hae Moon Hyeon
(74) *Attorney, Agent, or Firm* — Patterson Thuente Pedersen, P.A.

(57) ABSTRACT

Described herein is a cartridge for use with apparatus for heating smokable material to volatilize at least one component of the smokable material. The cartridge comprises a housing defining a chamber, smokable material located in the chamber, and a mass of thermal insulation material located between the smokable material and the housing. Also disclosed is apparatus for heating smokable material to volatilize at least one component of the smokable material. The apparatus comprises an assembly having an interface, and the cartridge, wherein the cartridge is for co-operating with the interface of the assembly.

23 Claims, 10 Drawing Sheets

(58) Field of Classification Search
USPC .................................................. 131/329, 328
See application file for complete search history.

(56) References Cited

U.S. PATENT DOCUMENTS

| | | | |
|---|---|---|---|
| 4,947,875 A | 8/1990 | Brooks | |
| 5,060,671 A | 10/1991 | Counts | |
| 5,065,776 A | 11/1991 | Lawson et al. | |
| 5,080,114 A * | 1/1992 | Rudolph | A24F 47/004 131/194 |
| 5,093,894 A | 3/1992 | Deevi et al. | |
| 5,095,921 A | 3/1992 | Losee | |
| 5,101,838 A | 4/1992 | Schwartz | |
| 5,135,009 A | 8/1992 | Muller | |
| 5,144,962 A | 9/1992 | Counts | |
| 5,179,966 A | 1/1993 | Losee et al. | |
| 5,322,075 A | 6/1994 | Deevi et al. | |
| 5,369,723 A | 11/1994 | Counts et al. | |
| 5,388,594 A | 2/1995 | Counts et al. | |
| 5,408,574 A | 4/1995 | Deevi | |
| 5,505,214 A | 4/1996 | Collins et al. | |
| 5,573,692 A | 11/1996 | Das | |
| 5,666,978 A | 9/1997 | Counts et al. | |
| 7,088,914 B2 | 8/2006 | Whittle | |
| 7,163,015 B2 | 1/2007 | Moffitt | |
| 8,074,644 B2 | 12/2011 | Hale | |
| 8,528,569 B1 * | 9/2013 | Newton | A61M 15/06 128/202.21 |
| 8,897,628 B2 | 11/2014 | Conley et al. | |
| 10,729,176 B2 * | 8/2020 | Vasiliev | A24F 47/008 |
| 2002/0078951 A1 | 6/2002 | Nicholes | |
| 2004/0234699 A1 * | 11/2004 | Hale | A61M 11/041 427/421.1 |
| 2006/0032501 A1 | 2/2006 | Hale et al. | |
| 2007/0102013 A1 | 5/2007 | Adams et al. | |
| 2008/0092912 A1 | 4/2008 | Robinson et al. | |
| 2008/0149121 A1 | 6/2008 | Wrenn et al. | |
| 2008/0126828 A1 | 9/2008 | Wensley | |
| 2008/0216828 A1 | 9/2008 | Wensley | |
| 2008/0302374 A1 | 12/2008 | Wengert et al. | |
| 2010/0031968 A1 * | 2/2010 | Sheikh | A24F 47/008 131/347 |
| 2011/0253135 A1 | 10/2011 | Hale et al. | |
| 2011/0277780 A1 | 11/2011 | Terry et al. | |
| 2011/0303231 A1 | 12/2011 | Li et al. | |
| 2012/0060853 A1 | 3/2012 | Robinson et al. | |
| 2012/0325227 A1 | 12/2012 | Robinson et al. | |
| 2013/0037041 A1 | 2/2013 | Worm et al. | |
| 2013/0042865 A1 | 2/2013 | Monsees et al. | |
| 2013/0125906 A1 * | 5/2013 | Hon | A24F 47/008 131/329 |
| 2013/0167853 A1 | 7/2013 | Liu | |
| 2013/0180525 A1 | 7/2013 | Cross | |
| 2013/1380525 | 7/2013 | Cross | |
| 2013/0192617 A1 * | 8/2013 | Thompson | A24F 47/008 131/329 |
| 2013/0192623 A1 | 8/2013 | Tucker | |
| 2013/0199528 A1 | 8/2013 | Goodman et al. | |
| 2013/0213419 A1 | 8/2013 | Tucker | |
| 2013/0220315 A1 | 8/2013 | Conley et al. | |
| 2013/0235227 A1 | 9/2013 | Chang et al. | |
| 2013/0255702 A1 * | 10/2013 | Griffith, Jr. | A24F 47/008 131/328 |
| 2013/0284192 A1 | 10/2013 | Peleg | |
| 2013/0284194 A1 * | 10/2013 | Newton | A24F 47/008 131/329 |
| 2013/0306084 A1 | 11/2013 | Flick | |
| 2013/0319431 A1 | 12/2013 | Cyphert et al. | |
| 2013/0319435 A1 | 12/2013 | Flick | |
| 2014/0020693 A1 | 1/2014 | Cochand | |
| 2014/0060554 A1 | 3/2014 | Collett | |
| 2014/0123989 A1 | 5/2014 | LaMothe | |
| 2014/0123992 A1 | 5/2014 | Thomas | |
| 2014/0130797 A1 | 5/2014 | Liu | |
| 2014/0182608 A1 * | 7/2014 | Egoyants | A24F 47/008 131/328 |
| 2014/0196718 A1 | 7/2014 | Li et al. | |
| 2014/0202476 A1 * | 7/2014 | Egoyants | A24F 47/008 131/329 |
| 2014/0261486 A1 | 9/2014 | Potter | |
| 2014/0261488 A1 | 9/2014 | Tucker | |
| 2014/0276739 A1 | 9/2014 | Brannan | |
| 2014/0299137 A1 | 10/2014 | Kieckbusch | |
| 2014/0334804 A1 | 11/2014 | Choi | |
| 2014/0366898 A1 | 12/2014 | Monsees | |
| 2015/0020827 A1 | 1/2015 | Liu | |
| 2015/0040925 A1 * | 2/2015 | Saleem | H05B 3/42 131/328 |
| 2015/0059780 A1 * | 3/2015 | Davis | A24F 40/42 131/328 |
| 2015/0090279 A1 * | 4/2015 | Chen | A24F 40/44 131/329 |
| 2015/0090280 A1 * | 4/2015 | Chen | A61M 15/06 131/329 |
| 2015/0150302 A1 | 6/2015 | Metrangolo | |
| 2015/0164143 A1 | 6/2015 | Maas | |
| 2015/0181934 A1 * | 7/2015 | Lyubomirskiy | A24F 40/46 131/329 |
| 2015/0181935 A1 * | 7/2015 | Lyubomirskiy | A24F 47/008 392/386 |
| 2015/0223520 A1 | 8/2015 | Phillips | |
| 2015/0296884 A1 * | 10/2015 | Liu | A24F 47/008 131/329 |
| 2015/0342258 A1 * | 12/2015 | Chen | H05B 3/06 131/329 |
| 2016/0007652 A1 | 1/2016 | Taluskie et al. | |
| 2016/0015081 A1 * | 1/2016 | Liu | H05B 3/16 131/329 |
| 2016/0044963 A1 | 2/2016 | Saleem | |
| 2016/0081394 A1 | 3/2016 | Alarcon et al. | |
| 2016/0198766 A1 | 7/2016 | Liu | |
| 2016/0295922 A1 | 10/2016 | John | |
| 2017/0055583 A1 * | 3/2017 | Blandino | H05B 6/108 |
| 2017/0055584 A1 * | 3/2017 | Blandino | H05B 6/36 |
| 2017/0119047 A1 * | 5/2017 | Blandino | A24D 1/20 |
| 2017/0119048 A1 * | 5/2017 | Kaufman | A24F 47/008 |
| 2017/0347711 A1 * | 12/2017 | Litten | A24F 47/008 |
| 2017/0347712 A1 * | 12/2017 | Singh | A24F 47/008 |
| 2017/0347713 A1 * | 12/2017 | Robinson | B32B 7/12 |
| 2018/0007972 A1 * | 1/2018 | Thorens | A61M 11/003 |
| 2018/0042302 A1 | 2/2018 | Robinson | |
| 2018/0070635 A1 | 3/2018 | Litten | |
| 2018/0228543 A1 | 8/2018 | Rooks | |
| 2018/0271151 A1 * | 9/2018 | Litten | H05B 1/0283 |
| 2018/0271153 A1 | 9/2018 | John | |
| 2018/0295887 A1 | 10/2018 | Cyphert | |
| 2018/0338520 A1 * | 11/2018 | Sutton | A24F 47/004 |

FOREIGN PATENT DOCUMENTS

| | | |
|---|---|---|
| CA | 2853569 | 5/2013 |
| CN | 1102964 | 5/1995 |
| CN | 1126425 A | 7/1996 |
| CN | 200983831 | 12/2007 |
| CN | 101268867 | 9/2008 |
| CN | 101925309 A | 12/2010 |
| CN | 202122097 | 1/2012 |
| CN | 102894485 | 1/2013 |
| CN | 202890467 | 4/2013 |
| CN | 202941412 | 5/2013 |
| CN | 103169157 | 6/2013 |
| CN | 203040682 U | 7/2013 |
| CN | 203166473 | 8/2013 |
| CN | 203167304 | 8/2013 |
| CN | 103300482 A | 9/2013 |
| CN | 103338665 A | 10/2013 |
| CN | 203234035 | 10/2013 |
| CN | 103416852 A | 12/2013 |
| CN | 103445299 A | 12/2013 |
| CN | 203341010 | 12/2013 |
| CN | 203446526 | 2/2014 |
| CN | 203522284 U | 4/2014 |

(56) References Cited

FOREIGN PATENT DOCUMENTS

| | | |
|---|---|---|
| CN | 203538371 | 4/2014 |
| CN | 103783674 A | 5/2014 |
| CN | 203575657 U | 5/2014 |
| CN | 103829375 | 6/2014 |
| CN | 203632329 U | 6/2014 |
| CN | 103919279 A | 7/2014 |
| CN | 103960784 A | 8/2014 |
| CN | 104010529 A | 8/2014 |
| CN | 203748671 U | 8/2014 |
| CN | 104244751 A | 12/2014 |
| CN | 203969196 U | 12/2014 |
| CN | 104602555 A | 5/2015 |
| CN | 204599333 | 9/2015 |
| CN | 204861167 | 12/2015 |
| CN | 107223021 A | 9/2017 |
| EP | 0 418 465 A2 | 3/1991 |
| EP | 0430559 A2 | 6/1991 |
| EP | 043559 B1 | 10/1991 |
| EP | 0488488 A1 | 6/1992 |
| EP | 0509196 A1 | 10/1992 |
| EP | 0520231 A2 | 12/1992 |
| EP | 0532194 A1 | 3/1993 |
| EP | 0520231 A3 | 7/1993 |
| EP | 0640297 A1 | 3/1995 |
| EP | 0822760 A2 | 2/1998 |
| EP | 0 822 760 A1 | 6/2003 |
| EP | 1736065 A1 | 12/2006 |
| EP | 1781360 A1 | 5/2007 |
| EP | 2022349 A1 | 2/2009 |
| EP | 2 316 286 A1 | 5/2011 |
| EP | 2 338 361 A1 | 6/2011 |
| EP | 2 340 729 A1 | 7/2011 |
| EP | 2 340 730 A1 | 7/2011 |
| EP | 2 368 449 A1 | 9/2011 |
| EP | 2 412 396 A1 | 2/2012 |
| EP | 2 460 424 A1 | 6/2012 |
| EP | 2574247 | 4/2013 |
| EP | 2698070 A1 | 2/2014 |
| EP | 2 724 630 A1 | 4/2014 |
| EP | 2742814 A1 | 6/2014 |
| EP | 2724630 B1 | 4/2016 |
| EP | 3038481 B1 | 5/2018 |
| EP | 2412396 B1 | 6/2018 |
| FR | 2 985 886 | 7/2013 |
| FR | 2985886 B3 | 5/2014 |
| GB | 2504076 A | 1/2014 |
| GB | 2513627 | 11/2014 |
| JP | H02171174 A | 7/1990 |
| JP | H03232481 A | 10/1991 |
| JP | H05277191 A | 10/1993 |
| JP | H06315366 A | 11/1994 |
| JP | H07502188 A | 3/1995 |
| JP | 2014520542 A | 8/2014 |
| JP | 2014525237 A | 9/2014 |
| KR | 101011453 B1 | 1/2011 |
| KR | 20120104533 A | 9/2012 |
| RU | 103281 U1 | 4/2011 |
| RU | 116018 U1 | 5/2012 |
| WO | WO 94/06313 | 3/1994 |
| WO | WO-9823171 A1 | 6/1998 |
| WO | WO-9963844 A1 | 12/1999 |
| WO | WO 2006/047663 A2 | 5/2006 |
| WO | WO-2006047663 A3 | 6/2006 |
| WO | WO 2007/042941 A2 | 4/2007 |
| WO | WO 2006/022714 | 5/2007 |
| WO | WO-2007042941 A3 | 10/2007 |
| WO | WO 2010/145805 | 12/2010 |
| WO | WO2012043941 A1 | 1/2011 |
| WO | WO 2012/085203 A1 | 6/2012 |
| WO | WO 2012085205 | 6/2012 |
| WO | WO-2012142293 A2 | 10/2012 |
| WO | WO 2013/034454 | 3/2013 |
| WO | WO 2013/034459 | 3/2013 |
| WO | WO-2013034455 A1 | 3/2013 |
| WO | WO 2013034458 | 3/2013 |
| WO | WO-2013040193 A2 | 3/2013 |
| WO | WO 2013/083635 A1 | 6/2013 |
| WO | WO 2013/098395 A1 | 7/2013 |
| WO | WO 2013/098410 A2 | 7/2013 |
| WO | WO 2013098409 | 7/2013 |
| WO | WO 2013110210 | 8/2013 |
| WO | WO-2013131763 A1 | 9/2013 |
| WO | WO 2013/152873 | 10/2013 |
| WO | WO 2013155645 | 10/2013 |
| WO | WO-2014008646 A1 | 1/2014 |
| WO | WO-2013098410 A3 | 3/2014 |
| WO | WO 2014045024 A2 | 3/2014 |
| WO | WO-2014066730 A1 | 5/2014 |
| WO | WO 2014/147114 A1 | 9/2014 |
| WO | WO2013022936 | 9/2014 |
| WO | WO-2014183073 A1 | 11/2014 |
| WO | WO 2015/179388 A1 | 11/2015 |

OTHER PUBLICATIONS

Application and File History for U.S. Appl. No. 15/540,718, filed Jun. 29, 2017, inventors Robinson.
Application and File History for U.S. Appl. No. 15/540,748, filed Jun. 29, 2017, inventors Litten.
Application and File History for U.S. Appl. No. 15/540,761, filed Jun. 29, 2017, inventors Robinson.
International Search Report, International Application No. PCT/EP2016/0512727, dated Jul. 25, 2016, 4 pages.
Chinese Office Action, Application No. 201480073324.6, dated Aug. 23, 2018, 7 pages (18 pages with translation).
A Collection of Translated Essays in Smoking and Health, National Tobacco Industry Science and Technology Information Station, pp. 265-266 (Light Industry Press, Feb. 1986).
Li Dongguang, Practical Chemical Product Formulation and Preparation, China Textile Press (Mar. 2013, pp. 298-299).
English translation of Chinese Office Action, Application No. 201480073324.6, dated Apr. 8, 2018, 15 pages.
Chinese Search Report, Application No. 201480073324.6, dated Feb. 6, 2018, 2 pages.
Korean Office Action, Application No. 10-2016-7012761, dated Sep. 14, 2017, 25 pages.
Japanese Office Action, Application No. 2016-530896, dated Jun. 27, 2017, 6 pages.
Canadian Office Action, Application No. 2,929,379, dated Apr. 21, 2017, 5 pages.
philly.com, "Coming: A nearly smokeless cigarette R.J. Reynolds' process will heat tobacco rather than burn it," Posted on Sep. 15, 1987 Retrieved on Sep. 10, 2014.
International Search Report for corresponding International App No. PCT/GB2014/053384 dated Mar. 10, 2015; 5 pages.
Written Opinion for corresponding International App No. PCT/GB2014/053384 dated Mar. 10, 2015; 5 pages.
Australian Examination Report, Application No. 2015373527, dated Oct. 25, 2018, 10 pages.
Japanese Office Action and Search Report, Application No. 2017-552225, dated Jul. 17, 2018, 4 pages (8 pages with translation).
Korean Office Action, Application No. 10-2017-7018009, dated Jul. 13, 2018, 6 pages (12 pages with translation).
Wikipedia Entry 'Voltage regulator' Jul. 23, 2018, 12 pages.
Wikipedia Entry '78xx' Jul. 23, 2018, 4 pages.
Analog Devices High Precision 2.5 V IC Reference AD580, © 2004, 8 pages.
Copy of forum page showing Fig. 1, retrieved on Jan. 21, 2019, 37 pages.
Extract of Third Edition Practical Electronics for inventors; pp. 1, 8, 771-775—2013, 3rd Ed ISBN 978-0-07-177134-4.
Wikipedia Entry 'Decoupling capacitor', Jul. 23, 2018, 4 pages.
Japanese Office Action, Application No. 2017-552229, dated Jul. 17, 2018, 3 pages (7 pages with translation).
International Search Report and Written Opinion, Application No. PCT/EP2015/080594, dated Apr. 11, 2016, 10 pages.
International Search Report, International Application No. PCT/EP2015/080595, dated Mar. 21, 2016, 2 pages.

(56) References Cited

OTHER PUBLICATIONS

Written Opinion of International Searching Authority, International Application No. PCT/EP2015/080595, dated Mar. 21, 2016, 4 pages.
Third Party Observations, dated Aug. 3, 2018, application No. 15822926.0, 96 pages.
Japanese Office Action and Search Report, Application No. 2017-552227, dated Jul. 17, 2018, 4 pages.
Chinese Office Action, Application No. 201580076530.7, dated May 13, 2019, 23 pages.
International Search Report and Written Opinion, Application No. PCT/EP2015/080587, dated Mar. 18, 2016, 7 pages.
European Examination Report, Application No. 15821057.5, dated Jul. 10, 2019, 5 pages.
Chinese Office Action and Search Report, Application No. 201580076528.X, dated Apr. 30, 2019, 17 pages.
European Extended Search Report, Application No. 19209872.1, dated Mar. 31, 2020, 7 pages.
Application and File History for U.S. Appl. No. 15/540,731, filed Jun. 29, 2017, inventors Robinson, 377 pages.
Communication pursuant to Article 94(3) EPC for Application No. 20205061.3, dated Nov. 2, 2021, 6 pages.
European Extended Search Report for Application No. 20205061.3, dated Mar. 11, 2021, 10 pages.
Examination Report No. 2 dated May 26, 2021 for Australian Patent Application No. 2019219729, 3 pages.
Forum Page Showing Fig. 1, https://electronics.stackexchange.com/questions/77333/how-do-you-calculate-caps-for-voltage-regulator-circuit, Jan. 21, 2019, 37 pages.
International Preliminary Report on Patentability for Application No. PCT/EP2015/080585, dated Jul. 13, 2017, 7 pages.
International Preliminary Report on Patentability for Application No. PCT/EP2015/080589, dated Jul. 13, 2017, 11 pages.
International Preliminary Report on Patentability for Application No. PCT/EP2015/080595, dated Jul. 13, 2017, 6 pages.
International Preliminary Report on Patentability for Application No. PCT/EP2015/080587, dated Jul. 13, 2017, 6 pages.
International Search Report and Written Opinion for Application No. PCT/EP2015/080585, dated Apr. 22, 2016, 8 pages.
International Search Report for Application No. PCT/EP2015/080589, dated Apr. 15, 2016, 3 pages.
International Search Report for Application No. PCT/EP2016/051727, dated Jul. 25, 2016, 5 pages.
Office Action and Search Report dated Apr. 23, 2019 for Chinese Application No. 201580076561.2, 41 pages.
Office Action and Search Report dated Apr. 8, 2020 for Chinese Application No. 201580076566.5, 20 pages.
Office Action For Chinese Application No. 201580076566.5, dated Apr. 1, 2021, 15 pages.
Office Action for Japanese Application No. 2019-142660, dated Oct. 13, 2020, 4 pages.
Office Action For Korean Application No. 10-2019-7011713, dated Jan. 8, 2021, 13 pages.
Office Action dated Apr. 17, 2018 for Canadian Application No. 2971076, 5 pages.
Office Action dated Jul. 2, 2019 for Chinese Application No. 201580076568.4, 24 pages.
Office Action dated Apr. 21, 2017 for Canadian Application No. 2929379, 5 pages.
Office Action dated Apr. 24, 2019 for Chinese Application No. 201580076566.5, 29 pages.
Scherz P., et al., "Voltage Regulators and Power Supplies," Third Edition, Practical Electronics for inventors, Chapter 11, 2013, 7 pages.
Search Report for European Application No. 15821057.5, dated Jul. 10, 2019, 5 pages.
Search Report dated May 22, 2018 for Russian Application No. 201712271312, 4 pages.
Substantive Examination Report dated Jan. 28, 2021 for Malaysian Application No. PI 2017702300, 2 pages.
Written Opinion for Application No. PCT/EP2015/080589, dated Apr. 15, 2016, 9 pages.
Written Opinion of International Searching Authority for International Application No. PCT/EP2015/080594, dated Jul. 7, 2016, 5 pages.

* cited by examiner

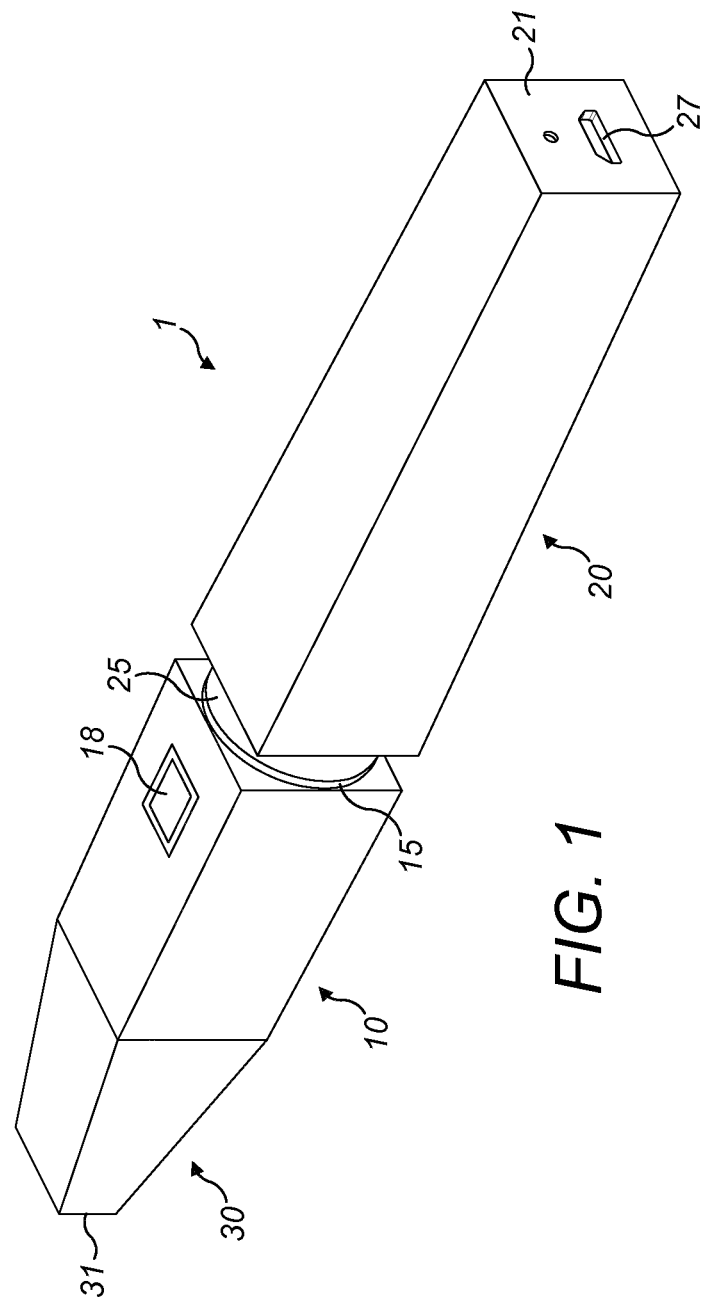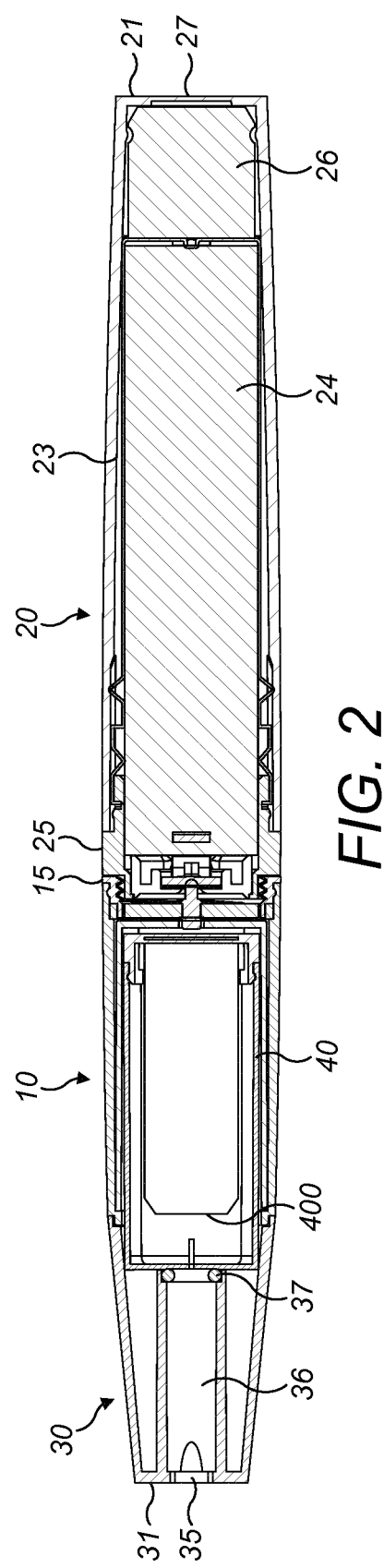

CARTRIDGE FOR HAVING A SLEEVE WITH SLOTS SURROUNDING A CONTACT PIECE WITH CORRESPONDING CONTACT ARMS

CROSS-REFERENCE TO RELATED APPLICATIONS

The present application is a National Phase entry of PCT Application No. PCT/EP2015/080595, filed Dec. 18, 2015, which claims priority from GB Patent Application No. 1423318.3, filed Dec. 29, 2014, each of which is hereby fully incorporated herein by reference.

TECHNICAL FIELD

The present disclosure relates to a cartridge for use with apparatus for heating smokable material, and to apparatus for heating smokable material.

BACKGROUND

Smoking articles such as cigarettes, cigars and the like burn tobacco during use to create tobacco smoke. Attempts have been made to provide alternatives to these articles by creating products that release compounds without combusting. Examples of such products are so-called "heat not burn" products or tobacco heating devices or products, which release compounds by heating, but not burning, material. The material may be, for example, tobacco or other non-tobacco products, which may or may not contain nicotine.

SUMMARY

According to a first aspect of the present disclosure, there is provided a cartridge for use with apparatus for heating smokable material to volatilize at least one component of the smokable material, the cartridge comprising: a housing defining a chamber; smokable material located in the chamber; and a mass of thermal insulation material located between the smokable material and the housing.

In an exemplary embodiment, the thermal insulation material encircles the smokable material.

In an exemplary embodiment, the thermal insulation material is in contact with the smokable material.

In an exemplary embodiment, the thermal insulation material fills a space between the smokable material and the housing.

In an exemplary embodiment, the smokable material comprises tobacco.

In an exemplary embodiment, the smokable material is in a solid state.

In an exemplary embodiment, the smokable material is bonded to the heating element. In an exemplary embodiment, the smokable material is bonded by an adhesive to the heating element.

In an exemplary embodiment, the thermal insulation material is in contact with the housing.

In an exemplary embodiment, the thermal insulation material comprises one or more materials selected from the group consisting of: wadding, fleece, non-woven material, non-woven fleece, woven material, knitted material, nylon, foam, closed cell foam, polystyrene, closed cell polystyrene foam, polyester, polyester filament, polypropylene, and a blend of polyester and polypropylene.

In an exemplary embodiment, the thermal insulation material comprises wadding or fleece and has a density of from about 60 to about 140 gsm. In an exemplary embodiment, the thermal insulation material has a density of from about 80 to about 120 gsm.

In an exemplary embodiment, the cartridge has an asymmetric exterior cross-sectional shape.

According to a second aspect of the present disclosure, there is provided a cartridge for use with apparatus for heating smokable material to volatilize at least one component of the smokable material, the cartridge comprising: a housing defining a chamber; a heating element located in the chamber; and a mass of thermal insulation material located between the heating element and the housing.

In an exemplary embodiment, the thermal insulation material encircles the heating element.

In an exemplary embodiment, the heating element is heatable by passing an electric current through the heating element. In an exemplary embodiment, the cartridge comprises two electrically-conductive terminals that are accessible from an exterior of the cartridge, wherein the heating element is electrically connected across the electrically-conductive terminals.

In an exemplary embodiment, smokable material is arranged on the heating element, the thermal insulation material being located between the smokable material and the housing.

In an exemplary embodiment, the thermal insulation material is in contact with the smokable material.

In an exemplary embodiment, the thermal insulation material fills a space between the smokable material and the housing.

In an exemplary embodiment, the smokable material comprises tobacco.

In an exemplary embodiment, the smokable material is in a solid state.

In an exemplary embodiment, the smokable material is bonded to the heating element. In an exemplary embodiment, the smokable material is bonded by an adhesive to the heating element.

In an exemplary embodiment, the thermal insulation material is in contact with the housing.

In an exemplary embodiment, the thermal insulation material comprises one or more materials selected from the group consisting of: wadding, fleece, non-woven material, non-woven fleece, woven material, knitted material, nylon, foam, closed cell foam, polystyrene, closed cell polystyrene foam, polyester, polyester filament, polypropylene, and a blend of polyester and polypropylene.

In an exemplary embodiment, the thermal insulation material comprises wadding or fleece and has a density of from about 60 to about 140 gsm. In an exemplary embodiment, the thermal insulation material has a density of from about 80 to about 120 gsm.

In an exemplary embodiment, the cartridge has an asymmetric exterior cross-sectional shape.

According to a third aspect of the present invention, there is provided apparatus for heating smokable material to volatilize at least one component of the smokable material, the apparatus comprising an assembly having an interface, and a cartridge according to the first or second aspect of the present invention, wherein the cartridge is for co-operating with the interface of the assembly.

In an exemplary embodiment, the apparatus is arranged to heat the smokable material to volatilize the at least one component of the smokable material without combusting the smokable material when the cartridge is co-operating with the interface of the assembly.

In an exemplary embodiment, the assembly comprises a controller for controlling the supply of electrical power to the heating element from an electrical power source when the cartridge is co-operating with the interface of the assembly.

In an exemplary embodiment, the assembly comprises a controller arranged to control heating of the heating element so as to cause heating of the smokable material to volatilize the at least one component of the smokable material without combusting the smokable material when the cartridge is co-operating with the interface of the assembly.

In an exemplary embodiment, the cartridge is able to co-operate with the interface in only one orientation relative to the assembly.

In an exemplary embodiment, the assembly comprises a recess for receiving at least a portion of the cartridge. In an exemplary embodiment, the recess has an interior cross-sectional shape corresponding to an exterior cross-sectional shape of the cartridge.

BRIEF DESCRIPTION OF THE DRAWINGS

Embodiments of the disclosure will now be described, by way of example only, with reference to the accompanying drawings, in which:

FIG. 1 shows a perspective view of an example of an apparatus for heating smokable material to volatilize at least one component of the smokable material.

FIG. 2 shows a schematic cross-sectional view of the apparatus of FIG. 1.

DETAILED DESCRIPTION

Figure 3:
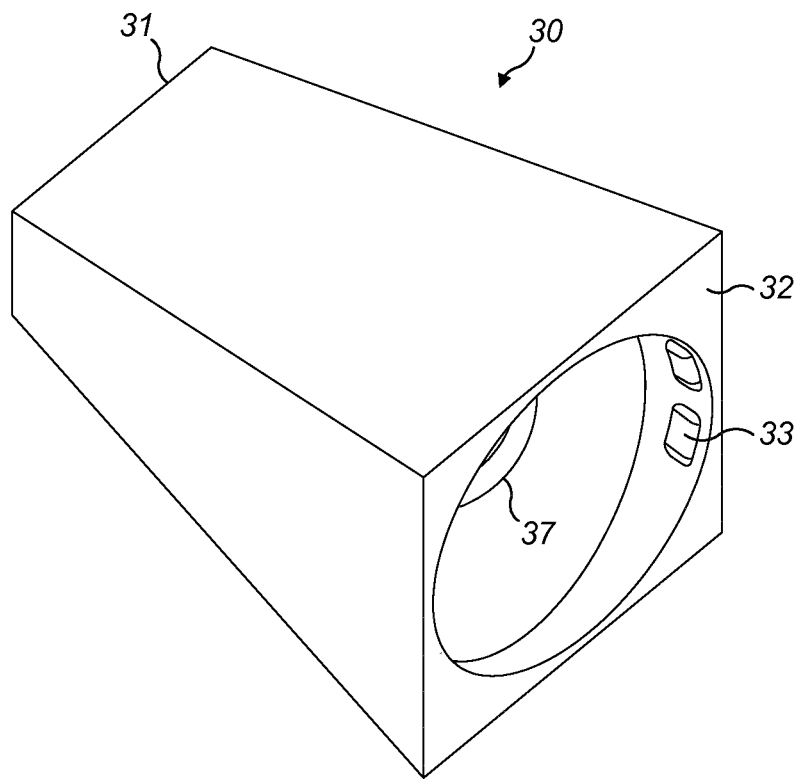
FIG. 3 shows a perspective view of a mouthpiece of the apparatus of FIG. 1 when detached from the rest of the apparatus.

As used herein, the term "smokable material" includes materials that provide volatilized components upon heating, typically in the form of an aerosol. "Smokable material" may be a non-tobacco-containing material or a tobacco-containing material. "Smokable material" may, for example, include one or more of tobacco per se, tobacco derivatives, expanded tobacco, reconstituted tobacco, tobacco extract, homogenized tobacco or tobacco substitutes. The smokable material can be in the form of ground tobacco, cut rag tobacco, extruded tobacco, gel or agglomerates. "Smokable material" also may include other, non-tobacco, products, which, depending on the product, may or may not contain nicotine.

As used herein, "polysaccharides" encompasses polymeric carbohydrate molecules composed of long chains of monosaccharide units bound together by glycosidic linkages, and salts and derivatives of such compounds. Suitably, derivatives of such compounds may have ester, ether, acid, amine, amide, urea, thiol, thioether, thioester, thiocarboxylic acid or thioamide side groups on the monosaccharide units. Example polysaccharides include cellulose and cellulose derivatives and alginic acid and salts thereof. In some embodiments, the polysaccharide may adhere the smokable material to the heating element. In other embodiments, the adhesive may comprise the polysaccharide as an adhesion promoter.

As used herein, "cellulose derivatives" are compounds in which the hydroxyl groups of cellulose are partially or fully substituted by various groups. Example cellulose derivatives are cellulose esters and ethers. In some embodiments, the cellulose derivative may comprise a cellulose ether, which may include alkyl, hydroxyalkyl and carboxyalkyl cellulose ethers. In some embodiments, the cellulose derivative may be a hydroxyalkyl cellulose ether, such as hydroxyethyl cellulose, hydroxypropyl cellulose, hydroxyethyl methylcellulose, hydroxypropyl methylcellulose and hydroxyethyl ethylcellulose. The cellulose derivative may be selected from hydroxyethyl methylcellulose, hydroxypropyl methylcellulose and hydroxyethyl ethylcellulose in some cases. The cellulose derivative may comprise or substantially consist of hydroxypropyl methylcellulose.

As used herein, "polyimide" refers to any polymer comprising or substantially formed of imide monomers and may be saturated or unsaturated. The polyimide may be hydrophobic.

As used herein, "polyester" refers to polymers which contain the ester functional group in their main chain. They may be formed by the esterification condensation of polyfunctional alcohols and acids. In some cases, the ester functional group is present about half or the repeating units, or in the majority of or substantially all of the repeating units. Polyesters may be saturated or unsaturated, aliphatic, semi-aromatic or aromatic, and may be copolymers or homopolymers. The polyester may be hydrophobic.

As used herein, the terms "flavor" and "flavorant" refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, or powder.

Referring to FIGS. 1 and 2, there is shown a perspective view and a schematic cross-sectional view of an example of an apparatus 1 for heating smokable material to volatilize at least one component of the smokable material. The apparatus 1 is arranged to heat smokable material to volatilize at least one component of the smokable material, typically to form an aerosol which can be inhaled, without combusting, or burning, the smokable material. The apparatus 1 comprises a first casing portion 10, a second casing portion 20, a mouthpiece 30 and a cartridge 40. The combination of the first and second casing portions 10, 20 constitutes a casing of the apparatus 1. The combination of the first and second casing portions 10, 20 and the mouthpiece 30 constitutes an assembly having an interface (discussed below) with which the cartridge 40 is able to co-operate. Each of these components will be discussed in turn.

The first casing portion 10 is located between the second casing portion 20 and the mouthpiece 30. Each of the first and second casing portions 10, 20 and the mouthpiece 30 defines a respective portion of the outer casing of the overall apparatus 1. Accordingly, the outward appearance of the apparatus 1 is defined by the combination of the first and second casing portions 10, 20 and the mouthpiece 30.

Figure 5:
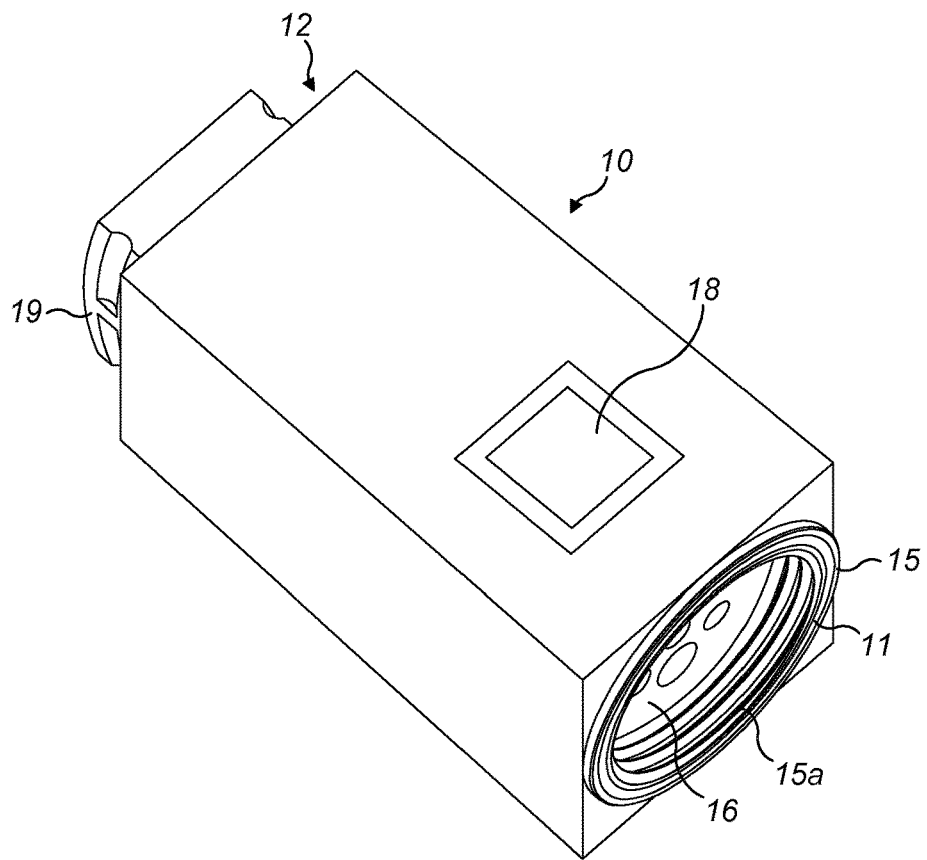
FIG. 5 shows a perspective view of a first casing portion of the apparatus of FIG. 1 when detached from the rest of the apparatus.
Figure 6:
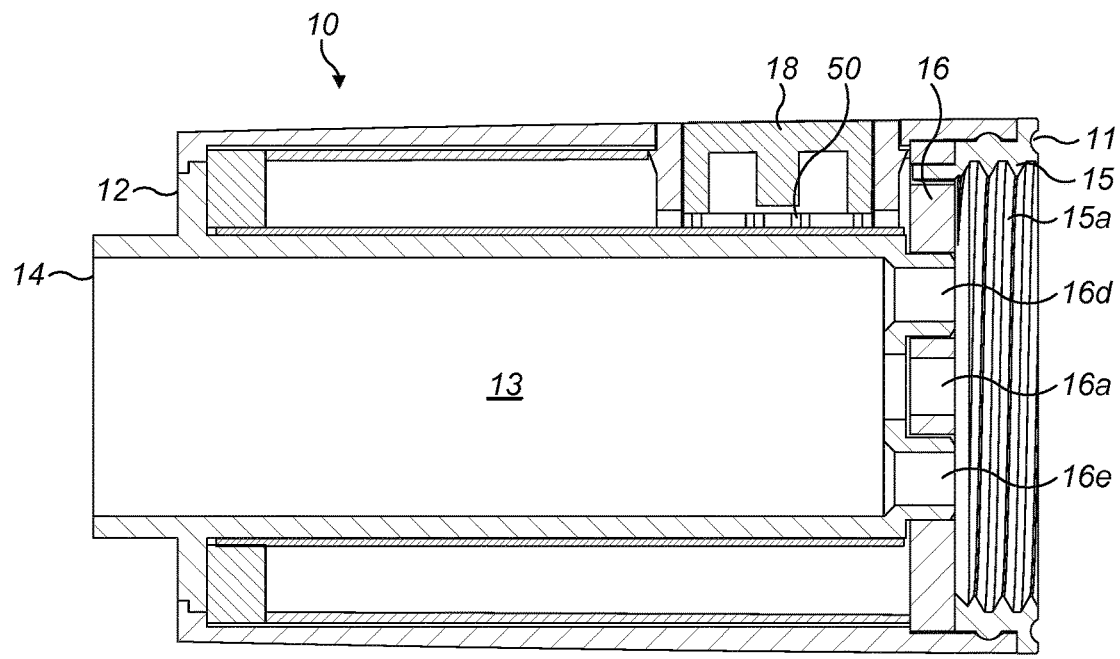
FIG. 6 shows a schematic cross-sectional view of the first casing portion of FIG. 5.

Referring to FIGS. 1, 5 and 6, the first casing portion 10 is generally tubular and elongate, has first and second opposite longitudinal ends 11, 12, and defines the interface for co-operating with the cartridge 40. In this embodiment, the interface comprises a recess 13 for receiving the cartridge 40. In other embodiments, the interface can take a different form, such as a shelf, a surface, or a projection, and optionally requires mechanical mating with the cartridge 40 in order to co-operate with the cartridge 40. The second longitudinal end 12 of the first casing portion 10 defines an opening 14 into the recess 13. The opening 14 is shaped and sized so that the cartridge 40 is movable through the opening 14 to allow a user to insert the cartridge 40 into the recess 13 and/or to remove the cartridge 40 from the recess 13, as will be described in more detail below. The first longitudinal end 11 of the first casing portion 10 comprises a first connector 15 that is releasably engageable with a second connector 25 of the second casing portion 20, as is also described in more detail below.

Referring to FIGS. 1, 2, 7 and 8, the second casing portion 20 is generally tubular and elongate, has first and second opposite longitudinal ends 21, 22, and defines a compartment 23. A plurality of first electrical components is contained in the compartment 23. The first electrical components in this embodiment comprise an electrical power source 24 in the form of a rechargeable battery, a printed circuit board (PCB) 26 and a universal serial bus (USB) charging interface 27. In other embodiments, the electrical power source 24 may be other than a rechargeable battery, such as a non-rechargeable battery or a capacitor. The charging interface 27 is accessible at the exterior of the apparatus 1 at the first longitudinal end 21 of the second casing portion 20. An electrical charging circuit and a voltage regulator 26b are provided on the PCB 26. The combination of the electrical charging circuit and the charging interface 27 constitutes a charging arrangement of the apparatus 1. The electrical charging circuit is electrically connected to positive and negative terminals 24a, 24b of the battery 24 and is electrically connected to the charging interface 27. The battery 24 is chargeable by connecting the charging arrangement to an external supply (not shown) of electrical power using the charging interface 27. The electrical charging circuit comprises an overcharge preventer for preventing overcharging of the battery 24. In variations to the illustrated embodiment, the charging interface 27 may take a form other than that dictated by the USB standard and/or may be located elsewhere on the second casing portion 20 or elsewhere on the apparatus 1. In some embodiments, the charging arrangement may be omitted.

Figure 7:
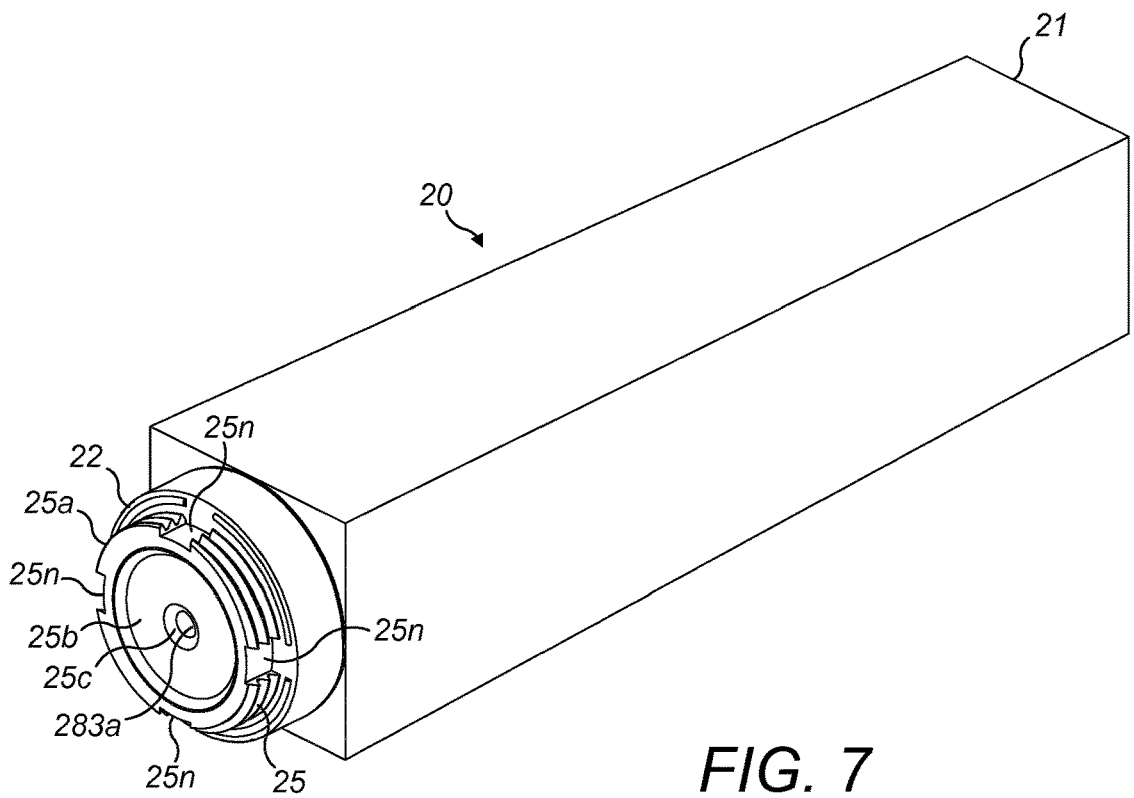
FIG. 7 shows a perspective view of a second casing portion of the apparatus of FIG. 1 when detached from the rest of the apparatus.
Figure 8:
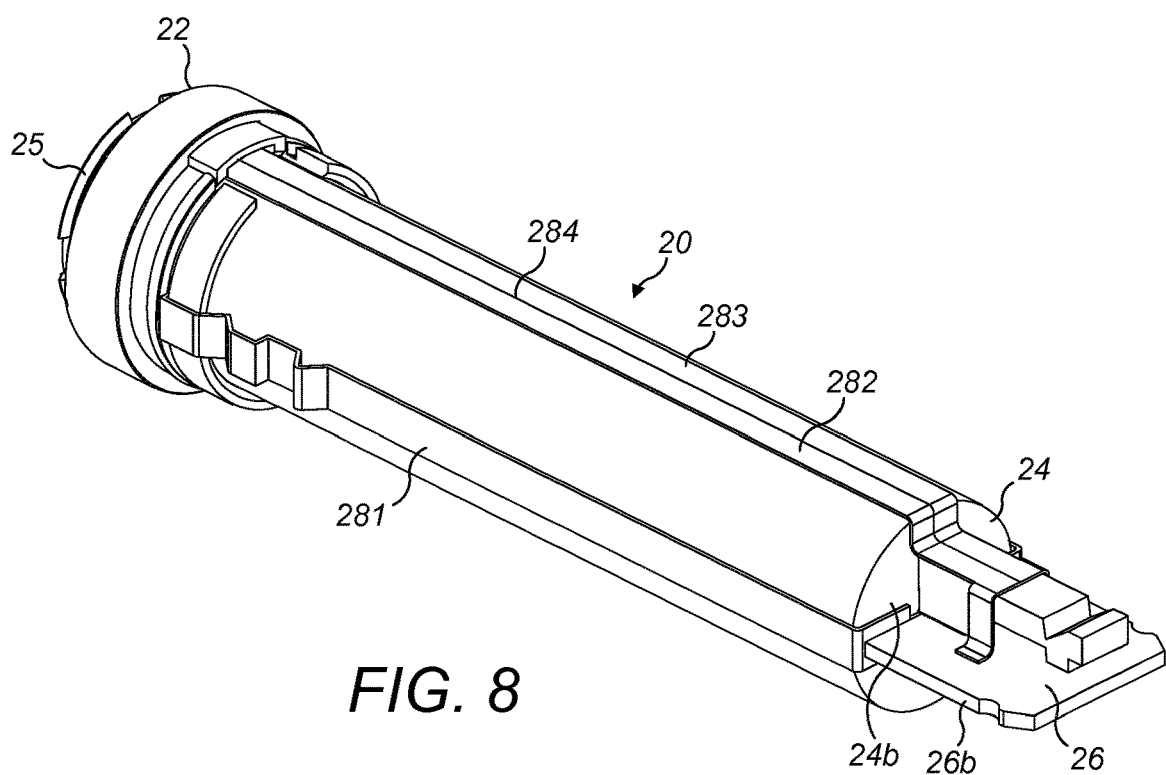
FIG. 8 shows another schematic perspective view of the second casing portion of FIG. 7 with a shell of the second casing portion that defines a compartment of the second casing portion removed.

Referring to FIG. 7, the second longitudinal end 22 of the second casing portion 20 comprises the second connector 25 that is engageable with the first connector 15 of the first casing portion 10. In this embodiment, the first connector 15 is engageable with the second connector 25 so as to connect the second casing portion 20 to the first casing portion 10. In other embodiments, the first and second casing portions 10, 20 may be permanently connected, such as through a hinge or flexible member, so that engagement of the first connector 15 with the second connector 25 would not connect the second casing portion 20 to the first casing portion 10, as such but would serve to facilitate partial separation or opening of the first casing portion 10 and the second casing portion 20. In this embodiment, the first connector 15 is releasably engageable with the second connector 25 so as to detachably connect the second casing portion 20 to the first casing portion 10. Accordingly, if the rechargeable battery 24 contained in the second casing portion 20 becomes exhausted, a user is able to swap the second casing portion 20 for another second casing portion 20 containing a non-exhausted electrical power source 24. The user is thus able to continue using the apparatus 1, for example during recharging of the first, exhausted rechargeable battery 24. In other embodiments, the first connector 15 may not be disengageable from the second connector 25 once the first and second connectors 15, 25 are connected to each other. In such other embodiments the second casing portion 20 becomes permanently connected to the first casing portion 10 on engagement of the first and second connectors 15, 25.

Referring to FIGS. 5 to 8, in this embodiment the first and second connectors 15, 25 are female and male connectors 15, 25, respectively, and comprise co-operable female and male screw threads 15a, 25a, respectively. In some other embodiments, the first and second connectors 15, 25 may be female and male connectors 15, 25, respectively, and may comprise co-operable female and male screw threads, respectively. In still further embodiments, the first and second connectors 15, 25 may comprise co-operable structures other than screw threads, such as a pin and slot together defining a bayonet coupling, a protrusion and a hole together defining a snap-fit connection, a plug and a socket, or the like.

In this embodiment, the first and second connectors 15, 25 are electrically-conductive so that, when the first and second connectors 15, 25 are engaged, an electric current can be conducted from the second connector 25 to the first connector 15, as discussed in more detail below. In this embodiment, each of the first and second connectors 15, 25 is made from a metal or a metal alloy, such as copper or stainless steel, etc. In other embodiments, one or both of the first and second connectors 15, 25 may be made from a different electrically-conductive material.

Referring to FIG. 7, it can be seen that in this embodiment the second screw thread 25a has four notches 25n therethrough, spaced circumferentially around the second screw thread 25a. In other embodiments, there may be more or fewer notches 25n through the second screw thread 25a. In this embodiment, each of the notches 25n extends linearly and radially through the second screw thread 25a. In other embodiments, the notch(es) 25n may extend radially and non-linearly through the second screw thread 25a, or linearly and non-radially through the second screw thread 25a, or non-linearly and non-radially through the second screw thread 25a. In this embodiment, the notches 25n are provided only through the second screw thread 25a. In other embodiments, there may be one or more notches additionally or alternatively provided through the first screw thread 15a. In some embodiments, the first and second connectors 15, 25 may be arranged so that the notch(es) provided through the first screw thread 15a align with the notch(es) provided through the second screw thread 25a when the first connector 15 is fully engaged with the second connector 25.

Figure 11:
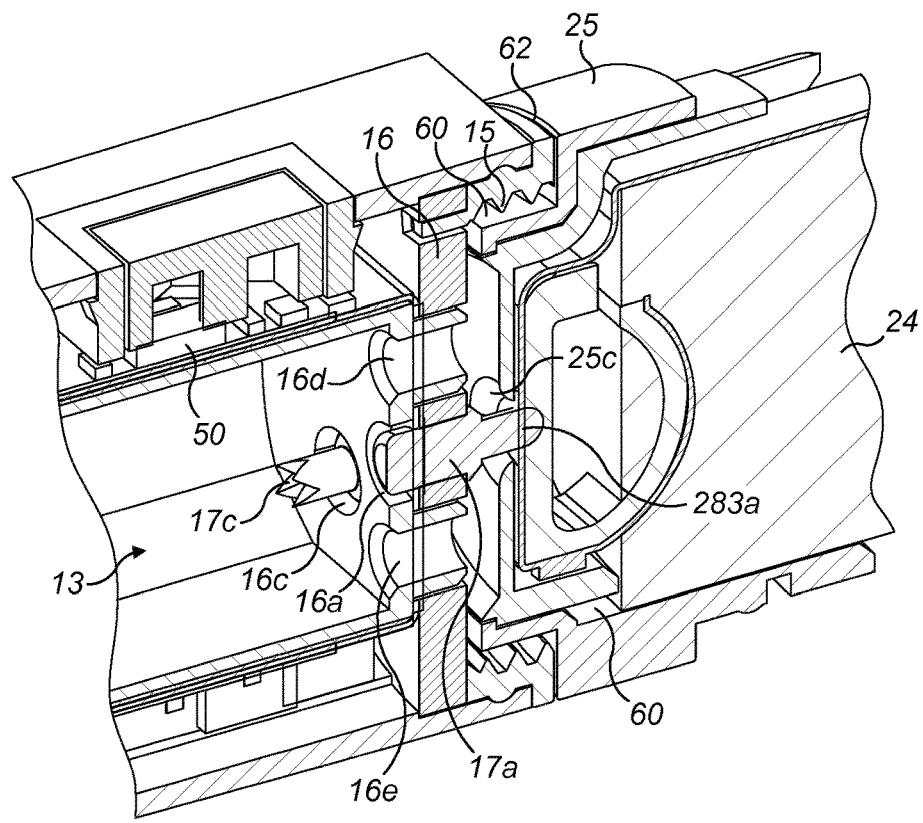
FIG. 11 shows a schematic perspective cross-sectional view of a portion of the apparatus of FIGS. 1 and 2.

When the first connector 15 is fully engaged with the second connector 25, as shown most clearly in FIG. 11, the first and second connectors 15, 25 cooperate to define between the first and second connectors 15, 25 four inlets 60 for admitting air into the apparatus 1, and more specifically into the recess 13 of the first casing portion 10, from an exterior of the apparatus 1. The inlets 60 fluidly communicate with the exterior of the apparatus 1 via an annular gap 62 that remains between the first and second connectors 15, 25 at an exterior surface of the apparatus 1 when the first connector 15 is fully engaged with the second connector 25. The first connector 15 is fully engaged with the second connector 25 when no more of the first connector 15 can be made to engage with the second connector 25. In this embodiment, this full engagement occurs when the first connector 15 cannot be moved further into the second connector 25. This may, for example, be because the leading edge of the first screw thread 15a of the first connector 15 has reached the end of the second screw thread 25a of the second connector 25, or because respective stops of the first and second connectors 15, 25 have been brought into contact with each other during the engagement of the first and second connectors 15, 25. In other embodiments, there may be provided other mechanisms for defining the point at which the first and second connectors 15, 25 are fully engaged. In this embodiment, the first and second connectors 15, 25 are relatively movable to alter a cross-sectional area of each of the inlets 60, while maintaining engagement of the first and second connectors 15, 25, so as to control the flow of air through the inlets 60. In this embodiment, the degree of engagement of the first and second connectors 15, 25 is changeable by rotating one of the first and second connectors 15, 25 relative to the other. This has the effect of correspondingly altering the axial dimension of the inlets 60 between the first and second connectors 15, 25, so as to alter the cross-sectional area of each of the inlets 60. In this embodiment, each of the inlets 60 is defined by a respective one of the notches 25n and a corresponding adjacent portion of the first connector 15. In other embodiments in which more or fewer notches are provided, there would be correspondingly more or fewer inlets, respectively.

Figure 9:
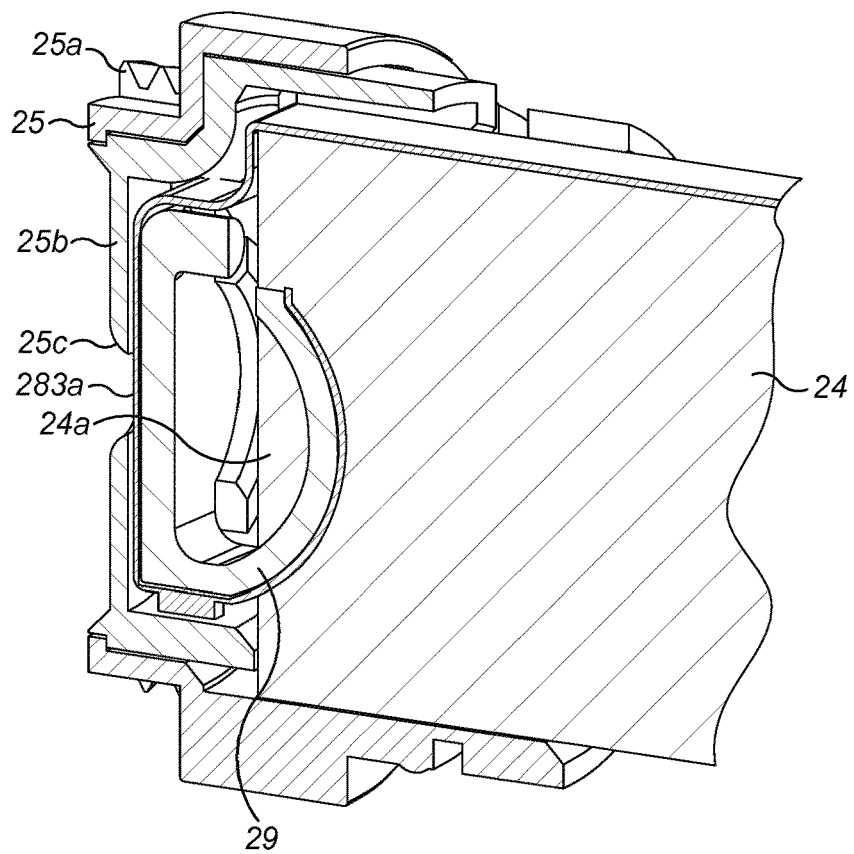
FIG. 9 shows a schematic perspective cross-sectional view of a portion of the second casing portion of FIG. 8.
Figure 10:
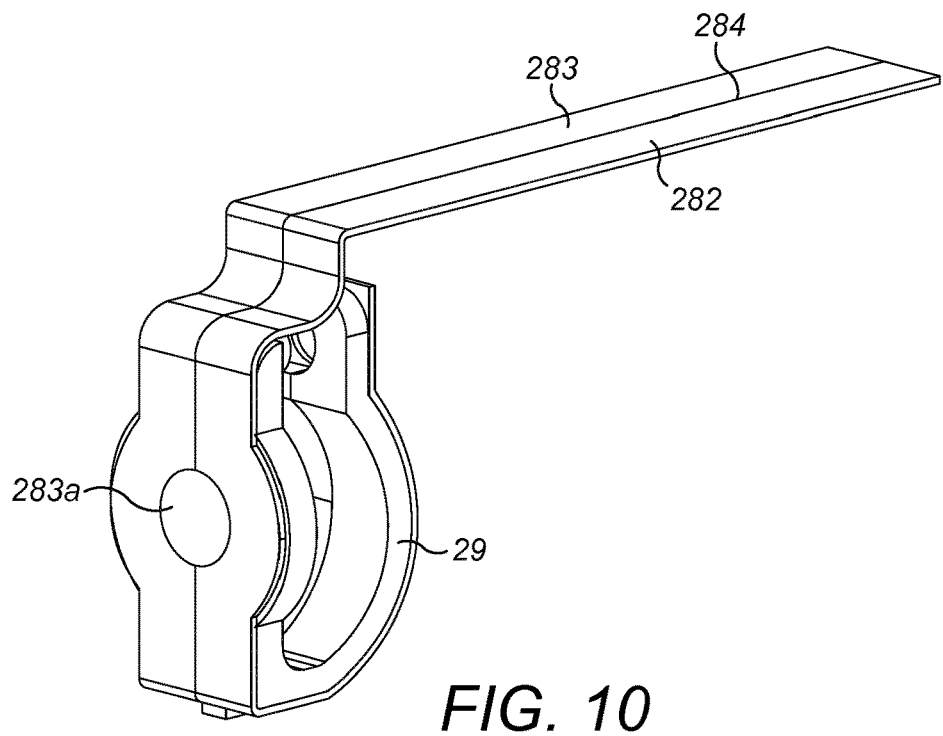
FIG. 10 shows a perspective view of, in isolation, a portion of a second electrical conductor of the second casing portion of FIGS. 8 and 9 around a resilient member.

In this embodiment, the compartment 23 provided in the second casing portion 20, and thus each of the first electrical components therein, is isolated from each of the inlets 60 by the material of the second connector 25, a board comprising second and third electrical conductors 282, 283 (discussed below and shown in FIGS. 9 and 10), and a plug 25b nested within the second connector 25 between the second connector 25 and the board. This helps prevent the first electrical components being brought into contact with dust or other foreign matter that might be drawn into the apparatus 1 through the inlet(s) 60 during operation of the apparatus 1, which otherwise could negatively affect performance of the first electrical components. However, in other embodiments, the compartment 23 and/or the electrical power source 24 and/or the PCB 26 (if provided) and/or the charging interface 27 (if provided) may be fluidly connected to one or more or all of the inlets.

In this embodiment, the first and second casing portions 10, 20 comprise respective electrical connections for supplying electrical power from the electrical power source 24 to the first casing portion 10, for powering the cartridge 40 as discussed below. More specifically, in this embodiment the second casing portion 20 comprises a first electrical conductor 281 (shown most clearly in FIG. 8) that extends from the negative terminal 24b of the battery 24 to the second screw thread 25a of the second connector 25 and bypasses the voltage regulator 26b, the second electrical conductor 282 (shown most clearly in FIGS. 9 and 10) that extends from the positive terminal 24a of the battery 24 to the voltage regulator 26b on the PCB 26, and a third electrical conductor 283 (also shown most clearly in FIGS. 9 and 10) that extends from the voltage regulator 26b to a terminal 283a. The third electrical conductor 283 is separated from the second electrical conductor 282 by an electrical insulator 284 so as to be electrically insulated from the second electrical conductor 282. The terminal 283a is centrally located on the longitudinal axis of the second casing portion 20 at the second longitudinal end 22 of the second casing portion 20. The terminal 283a is contactable via a hole 25c in the plug 25b. In this embodiment, the terminal 283a is a positive terminal of the second casing portion 20, and the second screw thread 25a of the second connector 25 is a negative terminal of the second casing portion 20.

A portion of the second electrical conductor 282 is in contact with the positive terminal 24a of the battery 24. A portion of the third electrical conductor 283 comprises the terminal 283a. These portions of the second and third electrical conductors 282, 283 are wrapped around a resilient member 29. The resilient member 29 biases the second electrical conductor 282 into contact with the positive terminal 24a of the battery 24 in a first direction. This helps to maintain good electrical contact between the second electrical conductor 282 and the positive terminal 24a of the battery 24. The resilient member 29 also biases the portions of the second and third electrical conductor 282, 283 into contact with the plug 25b in a second direction. This helps to provide a seal between the second and third electrical conductors 282, 283 and the plug 25b, thereby to aid isolation of the compartment 23 from the inlets 60. The second electrical conductor 282 extends from the positive terminal 24a of the battery 24, around the resilient member 29, and along the majority of the longitudinal length of the second casing portion 20 to the PCB 26, so as to electrically connect the positive terminal 24a of the battery 24 to the electrical charging circuit and the voltage regulator 26b on the PCB 26, as previously mentioned. The third electrical conductor 283 extends from the voltage regulator 26b and along the majority of the longitudinal length of the second casing portion 20 to the terminal 283a.

In this embodiment, each of the first, second and third electrical conductors 281, 282, 283 is made from a metal or a metal alloy, such as copper or stainless steel, etc., but in other embodiments one or more of the first, second and third electrical conductors 281, 282, 283 may be made from a different electrically-conductive material.

Figure 12:
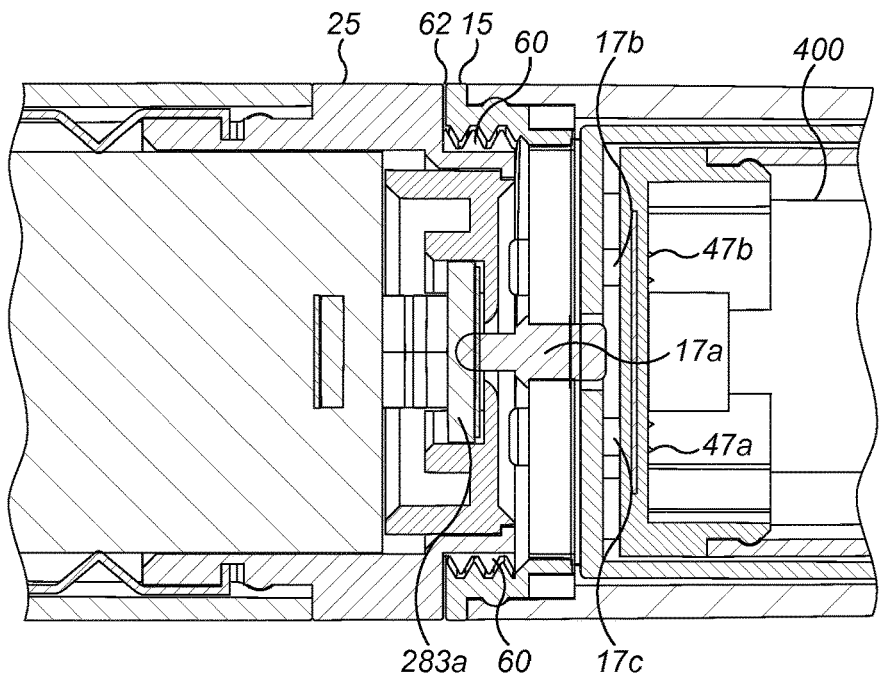
FIG. 12 shows a schematic cross-sectional view of a portion of the apparatus of FIGS. 1 and 2.
Figure 13:
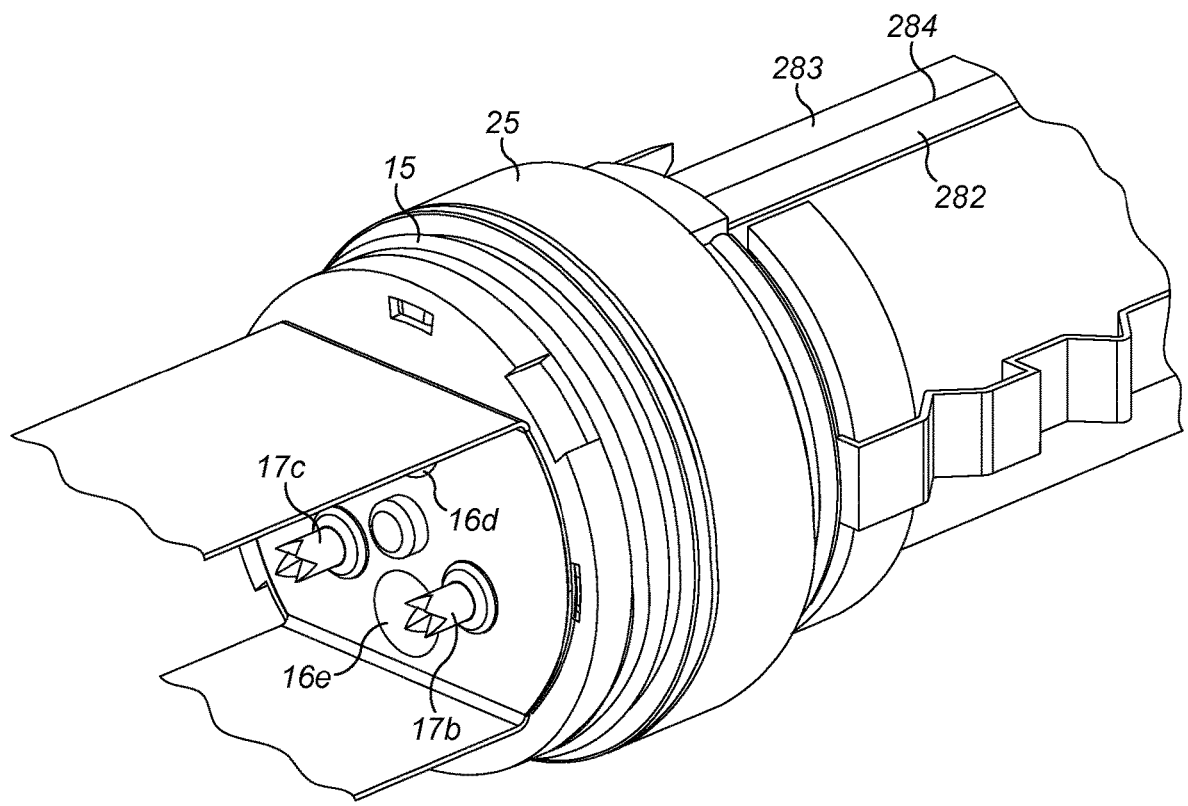
FIG. 13 shows a schematic perspective view of a portion of the apparatus of FIGS. 1 and 2 with portions thereof removed to expose second and third pins thereof.

The respective electrical connections of the first and second casing portions 10, 20 for supplying electrical power from the electrical power source 24 to the first casing portion 10 in the present embodiment are further illustrated in FIGS. 11 to 13. The first screw thread 15a of the first connector 15 is in this embodiment a negative terminal of the first casing portion 10, and is electrically connected to the negative terminal, i.e. the second screw thread 25a of the second connector 25, of the second casing portion 20 when the first connector 15 is fully engaged with the second connector 25. A plate 16 is mounted to the first connector 15. The plate 15 is circular about a central axis that is coincident with the longitudinal axis of the first casing portion 10. The plate 16 is within the first casing portion 10 between the first longitudinal end 11 of the first casing portion 10 and the recess 13 of the first casing portion 10. Five holes 16a-16e are provided through the plate 16. A first hole 16a of these holes is centrally located on the longitudinal axis of the first casing portion 10. Within the first hole 16a is a first pin 17a that projects away from the plate 16 towards the first longitudinal end 11 of the first casing portion 10. The first pin 17a is electrically-conductive and may be made from a metal or a metal alloy, such as copper or stainless steel or the like. The first pin 17a is a positive terminal of the first casing portion 10. When the first connector 15 is fully engaged with the second connector 25, as is most clearly illustrated in FIG. 11, the first pin 17a is located in the hole 25c in the plug 25b and is in surface contact with the positive terminal, i.e. the terminal 283a, of the second casing portion 20.

Referring to FIG. 12, within second and third holes 16b, 16c of the holes through the plate 16 are second and third pins 17b, 17c that project away from the plate 16 in an opposite direction to the pin 17a, and into the recess 13. Each of the second and third pins 17b, 17c is electrically-conductive and may be made from a metal or a metal alloy, such as copper or stainless steel or the like. Herein, the second pin 17b is referred to as a "first electrically-conductive terminal" and the third pin 17c is referred to as a "second electrically-conductive terminal". Moreover, herein, the first pin 17a is referred to as a "third electrically-conductive terminal", the terminal 283a of the second casing portion 20 is referred to as a "fourth electrically-conductive terminal", the first screw thread 15a of the first connector 15 is referred to as a "fifth electrically-conductive terminal", and the second screw thread 25a of the second connector 25 is referred to as a "sixth electrically-conductive terminal". The first and second electrically-conductive terminals 17b, 17c are for supplying electrical power to the cartridge 40, when the interface is co-operating with the cartridge 40 (i.e. when the cartridge 40 is fully located in the recess 13) and the first connector 15 is fully engaged with the second connector 25.

In this embodiment, the second electrically-conductive terminal 17c is electrically connected to the fifth electrically-conductive terminal 15a via a controller 50 contained in the first casing portion 10. Moreover, in this embodiment, the first electrically-conductive terminal 17b is electrically connected to the third electrically-conductive terminal 17a via the controller 50. In this embodiment, the controller 50 comprises an integrated circuit (IC). In other embodiments, the controller 50 may take a different form. The controller 50 is for controlling the supply of electrical power to a heating element 410 in the cartridge 40, when the cartridge 40 is fully located in the recess 13, as will be described in more detail below. When the first connector 15 is fully engaged with the second connector 25, the third electrically-conductive terminal 17a is in surface contact with the fourth electrically-conductive terminal 283a, and the fifth electrically-conductive terminal 15a is in surface contact with the sixth electrically-conductive terminal 25a. That is, the first casing portion 10 is connected to the second casing portion 20 with the third and fifth electrically-conductive terminals 17a, 15a in surface contact with the fourth and sixth electrically-conductive terminals 283a, 25a, respectively.

Accordingly, when the first connector 15 is fully engaged with the second connector 25, the positive terminal 24a of the electrical power source 24 is electrically connected to the controller 50 via the voltage regulator 26b, and the negative terminal 24b of the electrical power source 24 is electrically connected to the controller 50 by an electrically-conductive path that is free of the voltage regulator 26b. Since each of the first and second screw threads 15a, 25a is part of the casing of the apparatus 1, the electrically-conductive path comprises a part of the casing.

In this embodiment, the controller 50 is located in the first casing portion 10, and more specifically radially outwardly of the recess 13 and between the first and second longitudinal ends 11, 12 of the first casing portion 10. The controller 50 is operated in this embodiment by user-actuation of an actuator 18. The actuator 18 is located at the exterior of the first casing portion 10 radially outwardly of the controller 50 and the recess 13 and takes the form of a push-button. In other embodiments, a different form of actuator 18 may be provided, such as a toggle switch, a dial, or the like. In this embodiment, the controller 50 is isolated from each of the inlets 60 by the plate 16 and the section of the first casing portion 10 that defines the recess 13. In other embodiments, additional or alternative electrical components located in the first casing portion 10 may be isolated from the inlets 60. This helps prevent the electrical components in the first casing portion 10 being brought into contact with dust or other foreign matter that might be drawn into the apparatus 1 through the inlet(s) 60 during operation of the apparatus 1, which otherwise could negatively affect performance of those electrical components. However, in other embodiments, the controller 50 and/or other electrical components in the first casing portion 10 may be fluidly connected to one or more of the inlets 60.

In other embodiments, the controller 50 may be provided in the plate 16 of the first casing portion 10, or in the second casing portion 20. The controller 50 may be provided on a PCB or another structure. In embodiments in which the controller 50 is comprised in the second casing portion 20, one of the positive and negative terminals 24a, 24b of the electrical power source 24 may be electrically connected to the controller 50 via the voltage regulator 26b, and the other of the positive and negative terminals 24a, 24b of the electrical power source 24 may be electrically connected to the controller 50 by an electrically-conductive path that is free of the voltage regulator 26b.

In this embodiment, the first, third and fourth electrically-conductive terminals 17b, 17a, 283a are electrically connected to the positive terminal 24a of the electrical power source 24, and the second, fifth and sixth electrically-conductive terminals 17c, 15a, 25a are electrically connected to the negative terminal 24b of the electrical power source 24, when the first connector 15 is engaged with the second connector 25. In some other embodiments, the polarities of the terminals 24a, 24b of the battery 24 may be reversed.

Providing that one of the positive and negative terminals 24a, 24b of the electrical power source 24 is electrically connected to the controller 50 via the voltage regulator 26b, while the other of the positive and negative terminals 24a, 24b of the electrical power source 24 is electrically connected to the controller 50 by an electrically-conductive path that is free of the voltage regulator 26b, helps to simplify manufacture of the apparatus 1. Fewer connections to the voltage regulator 26b may be required and the electrically-conductive path can be provided regardless of the location of the voltage regulator 26b in the apparatus 1. This also gives a designer of the apparatus 1 greater design freedom when designing the apparatus 1.

Figure 4:
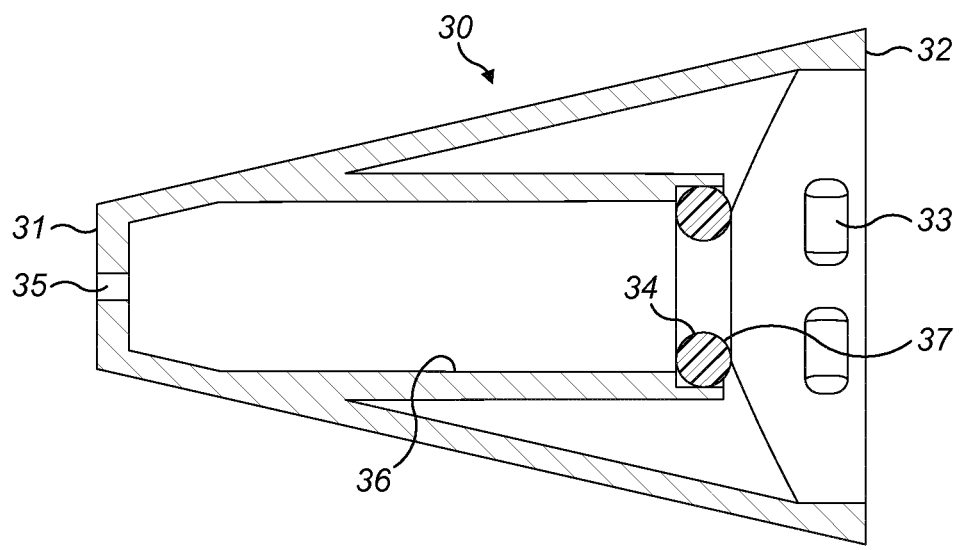
FIG. 4 shows a cross-sectional view of the mouthpiece of FIG. 3.

The mouthpiece 30 of this embodiment of the apparatus 1 will now be described in more detail, with particular reference to FIGS. 3 and 4. The mouthpiece 30 is generally tubular and elongate and has first and second opposite longitudinal ends 31, 32. The first longitudinal end 31 of the mouthpiece 30 is a first longitudinal end of the apparatus 1, whereas the first longitudinal end 21 of the second casing portion 20 is a second longitudinal end of the apparatus 1. The second longitudinal end 32 of the mouthpiece 30 comprises a connector 33 that is engageable with a second connector 19 of the first casing portion 10 at the second longitudinal end 12 of the first casing portion 10.

In this embodiment, the connector 33 of the mouthpiece 30 is engageable with the second connector 19 of the first casing portion 10 so as to connect the mouthpiece 30 to the first casing portion 10. In other embodiments, the mouthpiece 30 and the first casing portion 10 may be permanently connected, such as through a hinge or flexible member, so that engagement of the connector 33 of the mouthpiece 30 with the second connector 19 of the first casing portion 10 would not be so as to connect the mouthpiece 30 to the first casing portion 10, as such. In this embodiment, the connector 33 of the mouthpiece 30 is releasably engageable with the second connector 19 of the first casing portion 10 so as to detachably connect the mouthpiece 30 to the first casing portion 10. In other embodiments, the connector 33 of the mouthpiece 30 may not be disengageable from the second connector 19 of the first casing portion 10 once connected thereto. In such other embodiments the mouthpiece 30 may become permanently connected to the first casing portion 10 on engagement of the connector 33 of the mouthpiece 30 with the second connector 19 of the first casing portion 10.

In this embodiment, the connector 33 of the mouthpiece 30 and the second connector 19 of the first casing portion 10 respectively comprise two protrusions and two corresponding holes or recesses. The protrusions and recesses together define a snap-fit connection for connecting the mouthpiece 30 to the first casing portion 10. In other embodiments the connector 33 of the mouthpiece 30 and the second connector 19 of the first casing portion 10 may comprise other forms of co-operable structures, such as co-operable screw threads, a bayonet coupling, a plug and a socket, or the like.

The mouthpiece 30 comprises an inlet 34 at the second longitudinal end 32 of the mouthpiece 30, an outlet 35 at the first longitudinal end 31 of the mouthpiece 30, and a channel 36 fluidly connecting the inlet 34 with the outlet 35. In this embodiment, the channel 36 extends substantially linearly along the longitudinal axis of the mouthpiece 30. In other embodiments, the channel 36 may be located elsewhere in the mouthpiece 30 or may take other than a substantially linear form. The mouthpiece 30 also comprises a seal 37 surrounding the inlet 34. In this embodiment, the seal 37 defines the inlet 34, but in other embodiments the inlet 34 may be defined by another member and the seal 37 may surround the other member. In this embodiment, the seal 37 is flexible and resilient, but in other embodiments the seal 37 may be hard, rigid or inflexible. Moreover, in this embodiment the seal 37 comprises an O-ring that is attached to the rest of the mouthpiece 30, but in other embodiments the seal 37 could take a different form and may not even be circular. For example, in some embodiments, the seal 37 may be co-molded with the rest of the mouthpiece 30. In some such embodiments, the seal 37 may be resilient while other portions of the mouthpiece 30 are less resilient or inflexible.

In some embodiments, the mouthpiece 30 may comprise, or be impregnated with, a flavorant. The flavorant may be arranged so as to be picked up by the hot aerosol as the aerosol passes through the channel 36 of the mouthpiece 30 in use.

The mouthpiece 30 is locatable relative to the first casing portion 10 so as to cover the opening 14 into the recess 13. More specifically, in this embodiment, the mouthpiece 30 is locatable relative to the first casing portion 10 so as to cover the opening 14 with the outlet 35 at the exterior of the apparatus 1, and with the seal 37 facing the recess 13. When the mouthpiece 30 is so located relative to the first casing portion 10, the seal 37 is for contacting the cartridge 40 when the cartridge 40 is in the recess 13 to seal the inlet 31 of the mouthpiece 30 to the cartridge 40 in use. In this embodiment, when the mouthpiece 30 is so located relative to the first casing portion 10, and when the cartridge 40 is in the recess 13, the seal 37 is compressed between the channel 36 and the cartridge 40. This presses the cartridge 40 into the recess 13, which in turn helps ensure that the seventh and eighth electrically-conductive terminals 47a, 47b (discussed below) of the cartridge 40 are in surface contact with the first and second electrically-conductive terminals 17b, 17c, respectively.

Figure 14:
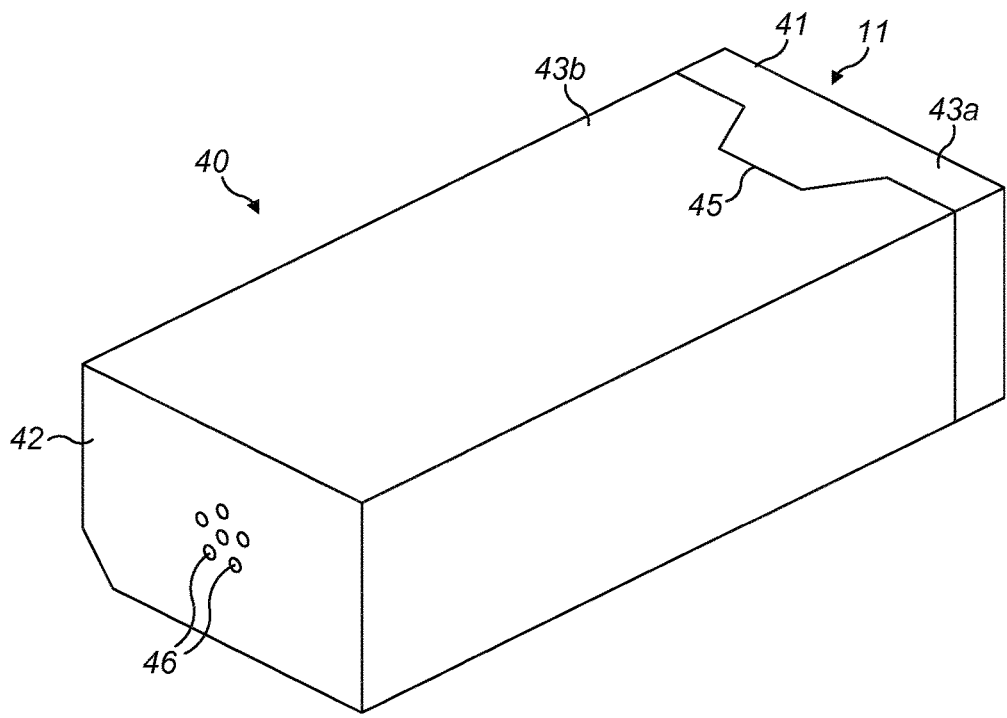
FIG. 14 shows a perspective view of, in isolation, a cartridge of the apparatus of FIG. 1.

The cartridge 40 of this embodiment of the apparatus 1 will now be described in more detail, with particular reference to FIGS. 14, 15 and 17. In this embodiment, the cartridge 40 comprises a housing 43 defining a chamber 44. A heating device 400 is located within the chamber 44. In other embodiments, the housing 43 may be omitted or take a different form to that illustrated. In some embodiments, the heating device may be comprised in an apparatus that does not comprise a cartridge. As will be described in more detail below, in this embodiment, the heating device 400 comprises a heating element 410 with smokable material 420 arranged on the heating element 410. The heating element 410, which is inaccessible to a user, is for heating the smokable material 420, and is a support on which the smokable material 420 is arranged. The heating device 400 is arranged to heat the smokable material 420 to volatilize at least one component of the smokable material 420 to create volatilized material. Typically, this volatilization causes the formation of an aerosol. The aerosol is inhalable by a user of the apparatus 1 via the channel 36 of the mouthpiece 30. Operation of the apparatus 1 will be described in more detail below.

In this embodiment, the housing 43 comprises first and second housing parts 43a, 43b that cooperate so as to define the chamber 44. The heating device 400 extends from the first housing part 43a into the chamber 44 and towards and through the second housing part 43b. The first and second housing parts 43a, 43b define first and second longitudinal ends 41, 42 of the cartridge 40, respectively. In other embodiments, first and second longitudinal ends 41, 42 of the cartridge 40 may both be defined by one housing part, i.e. by one component. In this embodiment, the first housing part 43a is non-unitary with the second housing part 43b and is attached to the second housing part 43b. In this embodiment, this attachment is effected through a snap-fit connection between the first and second housing parts 43a, 43b, but in other embodiments the attachment may be effected through other mechanisms. In this embodiment, all of the housing 43 is made of non-porous material. Accordingly, air is unable to pass through the material of the housing 43 itself. However, with the first and second housing parts 43a, 43b so attached, the first and second housing parts 43a, 43b cooperate so as to define an air flow path 45 in the form of a hole 45 between the first and second housing parts 43a, 43b. The air flow path 45 extends through the housing 43 and is for admitting air into the chamber 44 of the cartridge 40 from an exterior of the housing 43.

In other embodiments, the air flow path 45 may be defined differently, such as by a hole formed through a component of the housing 43. In some embodiments, the housing 43 may consist of more or fewer housing parts defining the chamber 44 and/or defining the air flow path 45. In embodiments other than those shown in the Figures, a portion, or all, of the housing 43 may be made of porous material for admitting air into the chamber 44 of the cartridge 40 from an exterior of the housing 43. That is, the air may be able to pass through the material of the housing 43 itself without there necessarily being a hole through the material or a gap between the first and second housing parts 43a, 43b. Accordingly, the porous material itself provides one or more air flow paths extending through the housing 43 for admitting air into the chamber 44 of the cartridge 40 from an exterior of the housing 43. In some embodiments, a first portion of the housing 43 may be made of porous material for admitting air into the chamber 44 from an exterior of the housing 43, and a second portion of the housing 43 may be made of non-porous material. In some such embodiments, the first portion and/or the second portion of the housing 43 may have one or more holes extending therethrough for further admitting air into the chamber 44 from an exterior of the housing 43.

Figure 16:
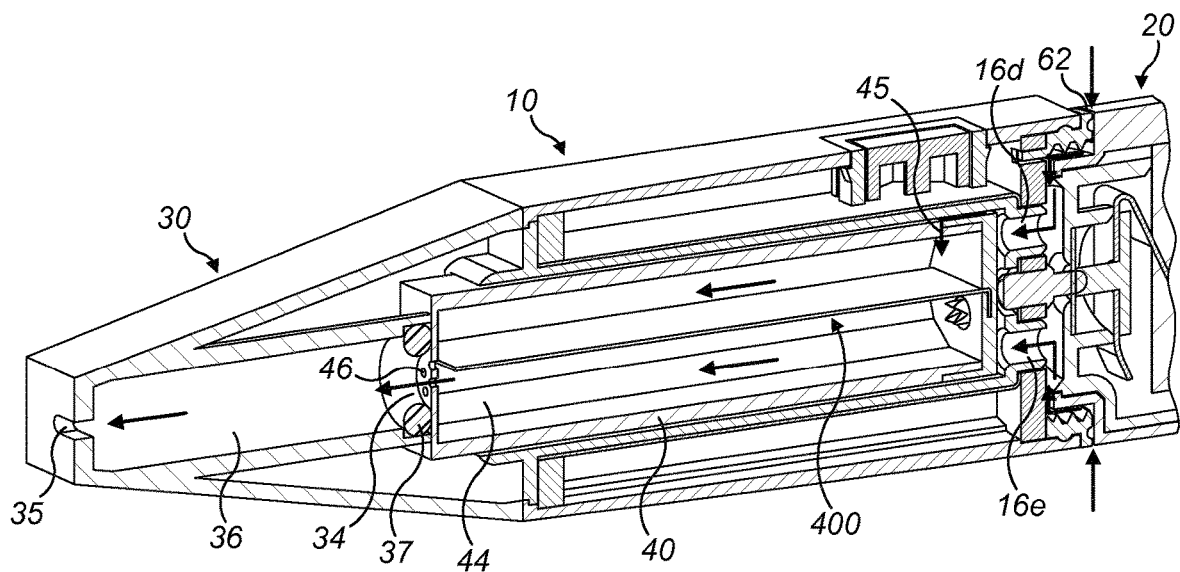
FIG. 16 shows another schematic perspective cross-sectional view of a portion of the apparatus of FIGS. 1 and 2 with an overall flow path therethrough indicated.

In this embodiment, since all of the housing 43 is made of non-porous material, aerosol or volatilized material generated within the housing 43 is unable to pass through the material of the housing 43 itself. However, the housing 43 has a plurality of volatilized material flow paths extending therethrough for permitting the volatilized material to pass from the chamber 44 out of the housing 43. In this embodiment, the volatilized material flow paths comprise a plurality of apertures 46 extending through the housing. In this embodiment, the apertures 46 extend through the second housing part 43b. As shown in FIGS. 2 and 16, in this embodiment, when the mouthpiece 30 is located relative to the first casing portion 10 so as to cover the opening 14, the seal 37 surrounds the apertures 46 at the exterior of the housing 43, with the apertures 46 fluidly connected to the channel 36 via the inlet 34 of the mouthpiece 30. In this embodiment, the apertures 46 are at the second longitudinal end 42 of the cartridge 40. The second longitudinal end 42 is closer to the mouthpiece 30 in the assembled apparatus 1 than is the first longitudinal end 41 of the cartridge 40. In some embodiments, the housing 43 may have only one volatilized material flow path extending therethrough for permitting the volatilized material to pass from the chamber 44 out of the housing 43. For example, in some embodiments, there may be provided only a single aperture in place of the plurality of apertures 46.

In embodiments other than those shown in the Figures, a portion, or all, of the housing 43 may be made of porous material for permitting aerosol or volatilized material to pass from the chamber 44 out of the housing 43. That is, aerosol or volatilized material may be able to pass through the material of the housing 43 itself without there necessarily being one or more apertures through the material. Accordingly, the porous material itself provides one or more volatilized material flow paths extending through the housing 43 for permitting the volatilized material to pass from the chamber 44 out of the housing 43. In some embodiments, a first portion of the housing 43 is made of non-porous material, and a second portion of the housing 43 is made of porous material for permitting volatilized material to pass from the chamber 44 out of the housing 43. The second portion of the housing 43 may comprise a plate co-molded with the first portion of the housing 43, for example. In some such embodiments, the first portion and/or the second portion of the housing 43 may have one or more apertures 46 extending therethrough for further permitting volatilized material to pass from the chamber 44 out of the housing 43. In some embodiments, an inlet portion of the housing 43 may be made of porous material for admitting air into the chamber 44 of the cartridge 40 from an exterior of the housing 43, and an outlet portion of the housing 43 may be made of porous material for permitting volatilized material to pass from the chamber 44 to the exterior of the housing 43. The inlet and outlet portions may have the same, or different, porosities or void fractions.

Where used, the porous material of the housing 43 may comprise for example polyethylene or nylon. Different grades of polyethylene offer different levels of porosity. The use of polyethylene to provide a suitable housing, or portion of a housing, for permitting aerosol or volatilized material to pass from the chamber 44 to the exterior of the housing 43 will be apparent to the skilled person on consideration of this disclosure. In some embodiments, part of the cartridge, such as the housing, may comprise, or be impregnated with, a flavorant. The flavorant may be arranged so as to be picked up by the hot aerosol generated within the chamber 44 in use.

Figure 17:
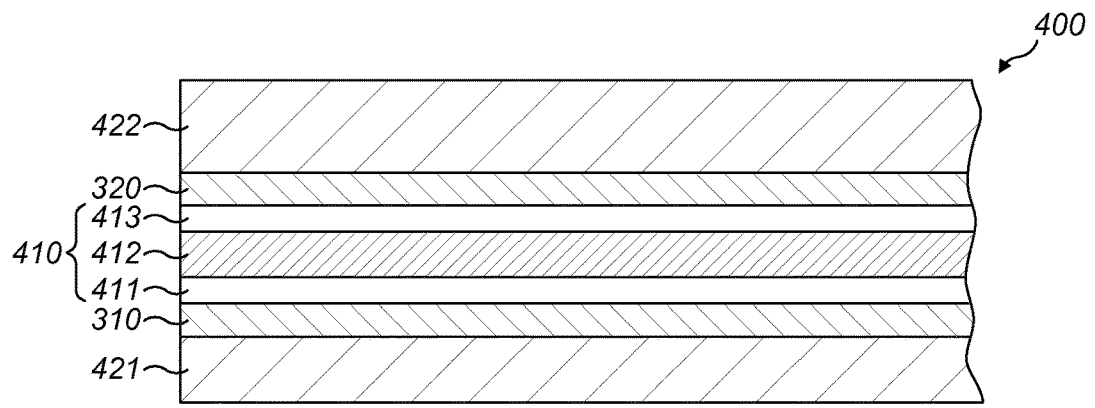
FIG. 17 shows a schematic close-up cross-sectional view of a portion of a heating device of the cartridge of FIG. 15.

In this embodiment, and as shown in FIG. 17, the heating element 410 comprises a sandwich or laminate structure comprising three layers. The three layers are a first layer 411 of material, a layer 412 of electrically-conductive material, and a second layer 413 of material. The layer 412 of electrically-conductive material is located between, and in contact with, the first and second layers 411, 413 of material. The first layer 411 of material is a first support layer 411, and the second layer 413 of material is a second support layer 413. However, in other embodiments, the sandwich or laminate structure may comprise more or fewer layers. In some embodiments, such as this embodiment, the heating element 410 comprises a first support layer 411 and a layer 412 of electrically-conductive material on a surface of the first support layer 411 and defining one or more electrically-conductive tracks. In some embodiments, the heating element 410 may not comprise a sandwich or laminate structure. For example, in some embodiments one or both of the first and second support layers 411, 413 may be omitted. In some embodiments, one or more additional layers may be provided between the layer 412 of electrically-conductive material and the first support layer 411 and/or between the layer 412 of electrically-conductive material and the second support layer 413.

The layer 412 of electrically-conductive material is retained relative to each of the first and second support layers 411, 413. This can be achieved in a number of different ways. For example, as in this embodiment, the material of the first and second support layers 411, 413 may envelop or surround the layer 412 of electrically-conductive material, so as to retain the layer 412 of electrically-conductive material relative to each of the first and second support layers 411, 413. Alternatively or additionally, some portion(s) of the material of the first and second support layers 411, 413 may be located in holes formed through the layer 412 of electrically-conductive material, so as to lock the first and second support layers 411, 413 to the layer 412 of electrically-conductive material. Alternatively or additionally, depending on the materials used, the material of the first and second support layers 411, 413 may bond naturally to the material of the layer 412 of electrically-conductive material, so as to lock the first and second support layers 411, 413 to the layer 412 of electrically-conductive material. Alternatively or additionally, the first and second support layers 411, 413 may be bonded to the layer 412 of electrically-conductive material by an adhesive. When provided, such adhesive may form additional identifiable adhesive layers between the layer 412 of electrically-conductive material and the first and second support layers 411, 413, respectively.

In this embodiment, the material of the first support layer 411 is the same material as the material of the second support layer 413. This can facilitate manufacture of the sandwich or laminate structure. During manufacture, the layer 412 of electrically-conductive material may be dipped in the material of the first and second support layers 411, 413 in fluid form, so as to coat some or all of the layer 412 of electrically-conductive material. Then, the material of the first and second support layers 411, 413 may be allowed to cure or set so as to harden, thereby retaining the resultant first and second support layers 411, 413 relative to the layer 412 of electrically-conductive material.

In this embodiment, the layer 412 of electrically-conductive material is a layer 412 of stainless steel. However, in other embodiments, the electrically-conductive material may be a different metal alloy, or a metal, or the like. For example, in some embodiments, the electrically-conductive material is, or comprises, one or more of: steel, stainless steel, copper and nichrome. In this embodiment, the electrically-conductive material is in the form of a foil, so that the layer 412 of electrically-conductive material is a foil layer 412. In embodiments in which the electrically-conductive material is other than stainless steel, the layer 412 of electrically-conductive material nevertheless may be a foil layer 412.

In this embodiment, the electrically-conductive material is etched in such a manner as to be patterned to provide the electrically-conductive tracks and to increase the surface area of the electrically-conductive material. For example, the patterning may cause the surface of the electrically-conductive material to be roughened or ridged or rippled or stippled, etc. In other embodiments, the electrically-conductive material may be printed in such a manner as to be patterned, or may be patterned by some other process. In still further embodiments, the electrically-conductive material may be non-patterned. For example, in some such embodiments, the layer 412 of electrically-conductive material may be a simple rectangular strip of the electrically-conductive material.

The electrically-conductive material of the heating element 410 is heatable by passing an electric current through the electrically-conductive material. By suitably patterning the electrically-conductive material, the surface area of the electrically-conductive material is increased so as to provide more area for heat conduction to the smokable material 420 arranged on the heating element 410. The first and second support layers 411, 413 may be so thin as not to fill completely the resultant roughened or patterned surface of the electrically-conductive material. The smokable material 420 may, for example, fill the resultant roughened or patterned surface of the heating element 410, so that the smokable material 420 has a higher surface area to volume ratio. In some embodiments, patterning of the electrically-conductive material can also act to set a cross sectional area and length of an electric current flow-path in the electrically-conductive material, so that heating of the heating element 410 can be achieved by passing a predetermined electric current through the electrically-conductive material. Moreover, by suitably patterning the electrically-conductive material, the electrically-conductive material can be shaped so that the electrically-conductive material is maintained at areas of the heating element 410 that are to be the focus of the heating. Accordingly, depending on the patterning provided, uniformity of heating of the smokable material 420 may be achieved in use.

In this embodiment, each of the first and second support layers 411, 413 is made of a material that is resistant to heat. In this embodiment, each of the first and second support layers 411, 413 is an electrical insulator. More particularly, each of these layers is resistant to heat at least over the expected range of temperatures of the heating element 410 that will arise in operation, such as for example 180 to 220 degrees Celsius. Polyimide is an example of material that is resistant to heat at least over this range of temperatures. In this embodiment, each of the first and second support layers 411, 413 is a layer of polyimide. As discussed elsewhere herein, the controller 50 is in some embodiments arranged to ensure that the heating element 410 is heated to a temperature within this range. Accordingly, the polyimide is able to withstand the heating of the electrically-conductive material during use of the device. In other embodiments, the material of the first support layer 411 may be other than polyimide, and/or the material of the second support layer 413 may be other than polyimide. In some embodiments, the first and second support layers 411, 413 are layers of respective different materials. However, whichever material or materials is/are used for the first and second support layers 411, 413, preferably the material(s) are resistant to heat at least over the above-discussed temperature range. In this embodiment, each of the first and second support layers 411, 413 is a layer that is impervious to moisture, to prevent any moisture present in the smokable material 420 from contacting the layer 412 of electrically-conductive material.

In this embodiment, the heating element 410 is planar, or at least substantially planar. A planar heating element 410 tends to be simpler to manufacture. However, in other embodiments, the heating element 410 may be non-planar. For example, in some embodiments, the heating element 410 may be folded, or crimped, or corrugated, or cruciform in cross section, or the like. A substantially cylindrical heater format is also envisaged. A non-planar heating element 410 can have an outer surface that is better suited to retaining the smokable material 420 thereon. For example, when a corrugated or similar heating element 410 is used, the smokable material 420 may adhere or bond more readily to troughs in the outer surface of the heating element 410 formed by the corrugations. Additionally, a non-planar heating element 410 provides more surface area for conduction of heat to the smokable material 420. It can then support more smokable material 420 in a layer of a given thickness. Smokable materials such as tobacco are often poor heat conductors and so it may be desirable to provide the smokable material 420 in relatively thin layers to reduce electrical power consumption or to increase the rate of heating the smokable material 420.

Figure 15:
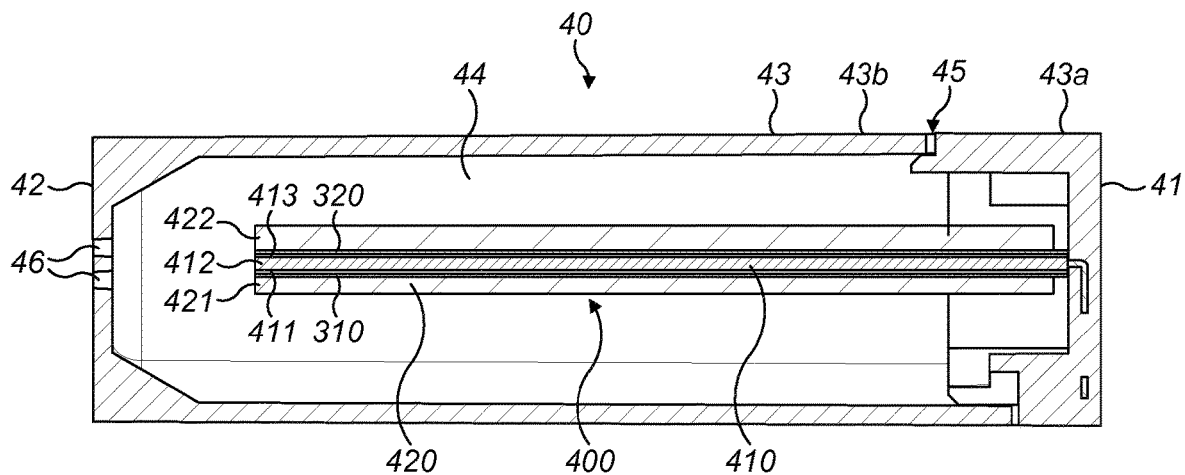
FIG. 15 shows a schematic cross-sectional view of the cartridge of FIG. 14.

In this embodiment, the smokable material 420 comprises tobacco and is arranged on the heating element 410 in two portions 421, 422, as shown in for example FIGS. 15 and 17. In this embodiment, the smokable material 420 is in a solid state and comprises particles of the smokable material. The first and second portions 421, 422 of the smokable material 420 are bonded by an adhesive to the heating element 410, as described in more detail herein. More specifically, the first portion 421 of the smokable material 420 is bonded to the first support layer 411 so that the first support layer 411 lies between the layer 412 of electrically-conductive material and the first portion 421 of the smokable material 420. The second portion 422 of the smokable material 420 is bonded to the second support layer 413 so that the second support layer 413 lies between the layer 412 of electrically-conductive material and the second portion 422 of the smokable material 420. Accordingly, the first and second portions 421, 422 of the smokable material 420 are arranged on first and second portions of the heating element 410, namely on respective surfaces of the first and second support layers 411, 413. In this embodiment, the respective surfaces are respective first and second sides of the heating element 410. Moreover, in this embodiment, the first and second sides are respective opposite sides of the heating element 410. In other embodiments, the first and second sides may be non-opposite sides of the heating element 410, such as adjacent sides of the heating element 410.

As shown in FIG. 17, in this embodiment the adhesive forms additional identifiable adhesive layers 310, 320 between the heating element 410 and the first and second portions 421, 422 of the smokable material 420, respectively. However, in some embodiments, the smokable material 420 may be interspersed within the adhesive so that the first and second portions 421, 422 of the smokable material 420 comprise the adhesive and no further identifiable adhesive layers are present. In some embodiments, the adhesive may be omitted and the smokable material 420 may be bonded to the heating element 410, or arranged on the heating element 410, by some other mechanism.

In some embodiments, the first portion 421 of the smokable material 420 has a form so as to be heatable by the heating element 410 more quickly than the second portion 422 of the smokable material 420. More specifically, in this embodiment for example, the first portion 421 of the smokable material 420 is arranged on the heating element 410 with a first thickness and the second portion 422 of the smokable material 420 is arranged on the heating element 410 with a second thickness. Thus, the first portion 421 of the smokable material 420 has the first thickness and the second portion 422 of the smokable material 420 has the second thickness. The second thickness is greater than the first thickness. Herein, in this context, "thickness" means a depth of the relevant portion 421, 422 of the smokable material 420 as measured from the surface of the heating element 410 on which the smokable material 420 is arranged in a direction normal to that surface.

In some embodiments, first and second portions 421, 422 of the smokable material 420 may be arranged on first and second portions of the heating element 410 that are first and second portions of one side of the heating element 410. That is, the first and second portions 421, 422 of the smokable material 420 may be on the same side of the heating element 410.

Figure 18:
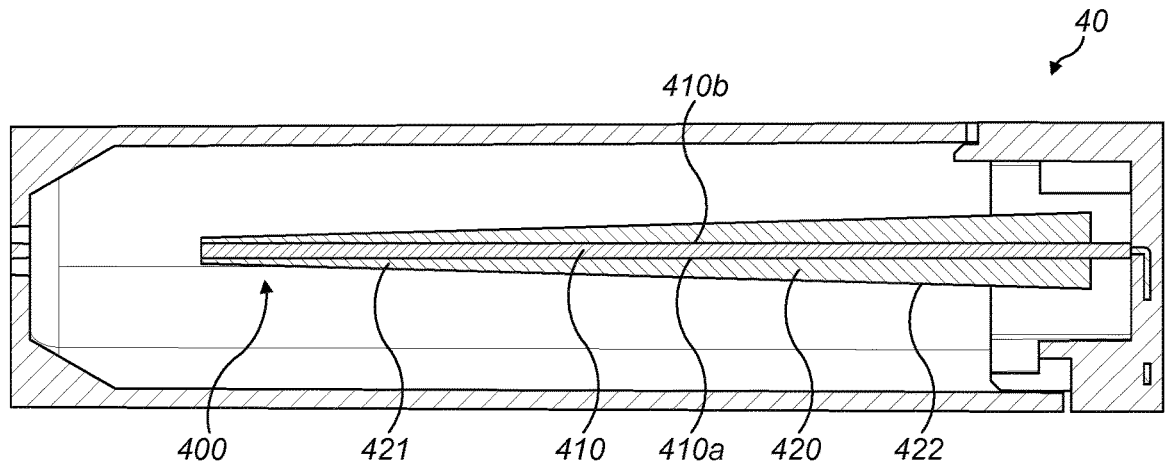
FIG. 18 shows a schematic cross-sectional view of a cartridge.

For example, as shown in the embodiment of FIG. 18, the smokable material 420 is arranged so that a first portion 421 of the smokable material 420 on a first side 410*a* of the heating element 410 has a first thickness and a second portion 422 of the smokable material 420 on the first side 410*a* of the heating element 410 has a second thickness. The second thickness is greater than the first thickness. A similar arrangement of the smokable material 420 is provided on a second side 410*b* of the heating element 410 opposite from the first side 410*a*.

Figure 19:
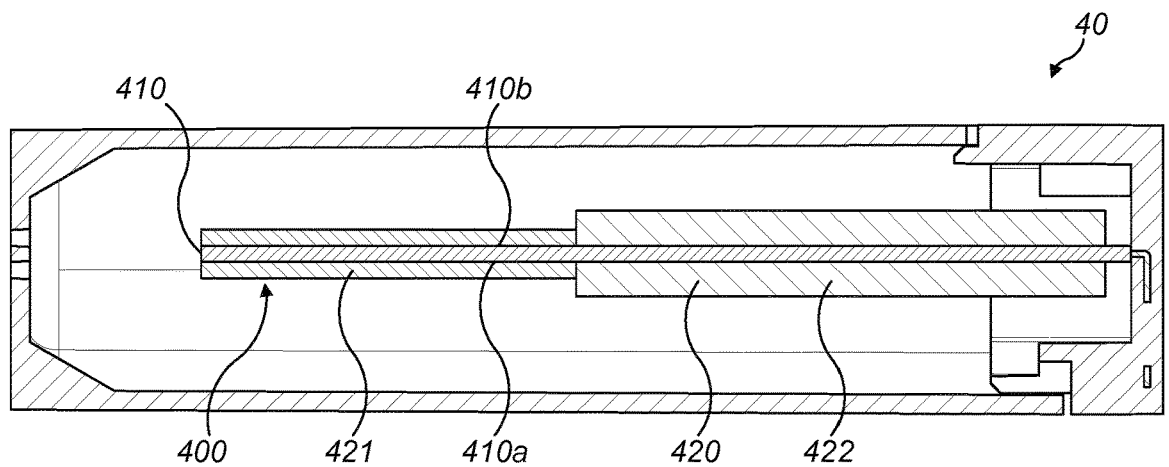
FIG. 19 shows a schematic cross-sectional view of a cartridge.
Figure 20:
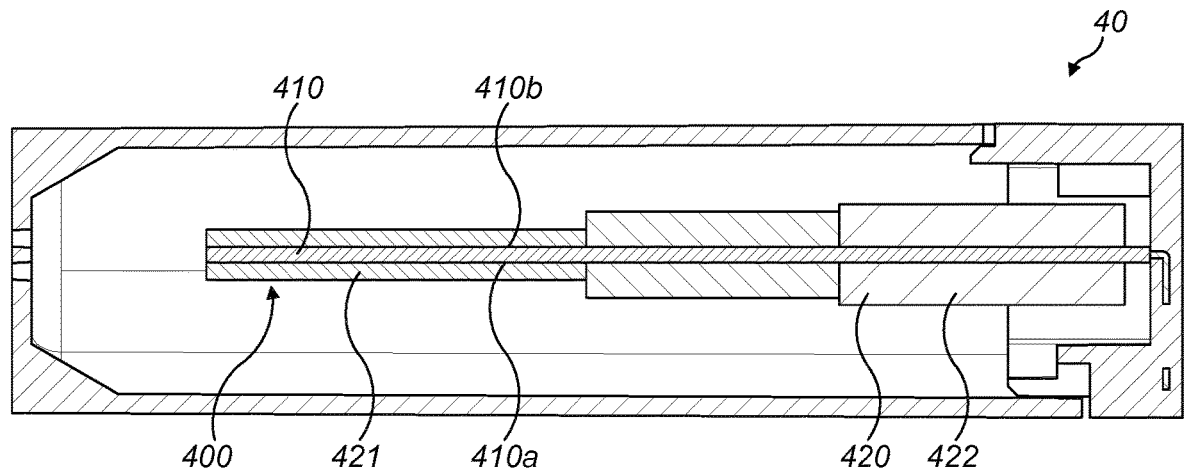
FIG. 20 shows a schematic cross-sectional view of a cartridge.

As shown in FIG. 18, the thickness of the smokable material 420 on the first side 410*a* of the heating element 410 tapers from the first portion 421 of the smokable material 420 to the second portion 422 of the smokable material 420. In this embodiment, the taper is linear or substantially linear. In other embodiments, the taper may be non-linear; for example, the outer surface of the smokable material 420 may be concave or convex. In still other embodiments, the smokable material 420 may be arranged on the first side 410*a* of the heating element 410 to a thickness that increases in a stepwise manner from the first portion 421 of the smokable material 420 to the second portion 422 of the smokable material 420. In one such embodiment, as shown in FIG. 19, there is only a single step in the thickness of the smokable material 420 arranged on the first side 410*a* of the heating element 410. The single step is at the point where the first portion 421 of the smokable material 420 meets the second portion 422 of the smokable material 420. In another such embodiment, as shown in FIG. 20, there are plural steps in the thickness of the smokable material 420 between the first and second portions 421, 422 of the smokable material 420 arranged on the first side 410*a* of the heating element 410. In the embodiment shown in FIG. 20, the first and second portions 421, 422 of the smokable material 420 are at respective opposite ends of the smokable material 420. However, in other embodiments, this may not be the case.

In some embodiments, the smokable material 420 may be arranged only on one side of the heating element 410. For example, in respective alternative embodiments to those shown in FIGS. 18 to 20, the smokable material 420 on the first side 410*a* or the second side 410*b* of the heating element 410 may be omitted.

By arranging different portions of the smokable material 420 on the heating element 410 with different thicknesses, progressive heating of the smokable material 420, and thereby progressive generation of aerosol, is achievable. More specifically, in use, only a relatively small degree of heating of the heating element 410 is required to cause the first, thinner portion 421 of the smokable material 420 to become heated, thereby to initiate volatilization of at least one component of the smokable material 420 in the first portion 421 of the smokable material 420 and formation of an aerosol in the first portion 421 of the smokable material 420. As the heating element 410 further heats up, the second, thicker portion 422 of the smokable material 420 becomes sufficiently heated to initiate volatilization of at least one component of the smokable material 420 in the second portion 422 of the smokable material 420 and formation of an aerosol in the second portion 422 of the smokable material 420. The aerosol is output from respective outer surfaces of the first and second portions 421, 422 of the smokable material 420. Accordingly, an aerosol is able to be formed relatively rapidly for inhalation by a user, and the heating device 400 is arranged to continue forming an aerosol thereafter for subsequent inhalation by the user even after the first, thinner portion 421 of the smokable material 420 may have ceased generating aerosol. The first portion 421 of the smokable material 420 may cease generating the aerosol when it becomes exhausted of volatilizable components of the smokable material 420.

In other embodiments, additionally or alternatively to the variation in thickness of the smokable material 420 in any of the above-described embodiments, the first and second portions 421, 422 of the smokable material 420 may have different mean particle sizes. That is, the first portion 421 of the smokable material 420 may comprise particles of the smokable material 420 having a first mean particle size, and the second portion 422 of the smokable material 420 may comprise particles of the smokable material 420 having a second mean particle size. The second mean particle size is greater than the first mean particle size. Typically, particles of the smokable material 420 having a smaller mean particle size are heatable more quickly by a given heat source than are particles of the smokable material 420 having a greater mean particle size. By providing different portions of the smokable material 420 with different mean particle sizes, progressive heating of the smokable material 420, and thereby progressive generation of aerosol, is achievable substantially as discussed above.

In some embodiments, the smokable material 420 may be provided having a mean particle size of 0.6 to 0.9 mm or 0.7 to 0.8 mm. Mean particle size can, however, vary across the smokable material. In some embodiments, the smokable material is prepared using mesh separation (or sieves) such that the majority or substantially all of the smokable material has a particle size in the above mentioned ranges. In some embodiments, a heater area of 6 $cm^2$ coated with such particulate smokable material 420 may provide an acceptable consumer experience lasting nominally three minutes. This size may, of course, be adjusted for a longer or shorter experience, as required. In some embodiments, the smokable material 420 may be in the form of a gel. The gel may or may not comprise particles of smokable material.

While in each of the above-described embodiments the smokable material 420 comprises a first portion 421 having a form so as to be heatable by the heating element 410 more quickly than a second portion 422 of the smokable material 420, in other embodiments this feature may be omitted.

The adhesive used to bond the smokable material 420 to the heating element 410 comprises a polysaccharide such as cellulose, a cellulose derivative, alginic acid or an alginate salt, suitably sodium, potassium or calcium alginate. In one embodiment, the adhesive comprises a cellulose derivative, suitably hydroxypropyl methyl cellulose (HPMC). In other embodiments, the adhesive used to bond the smokable material 420 to the heating element 410 comprises alginic acid or an alginate salt, suitably sodium, potassium or calcium alginate. Polysaccharides such as these demonstrate good wettability properties, which aid in bonding the smokable material 420 to the heating element 410. This is particularly the case when the adhesive is bonding smokable material 420 to a hydrophobic surface, such as a polyimide hydrophobic surface. It is also desirable that the adhesive be food acceptable and optionally, a food grade material.

In one embodiment, the identifiable adhesive layers 310, 320 between the heating element 410 and the smokable material 420 comprises a polysaccharide. The adhesive layers 310, 320 are disposed on, and substantially completely cover the support layers 411, 413. The adhesive may cover the heating element 410 at least partially. In other embodiments, the adhesive may be disposed directly on the electrically conductive material 12. In each case, the adhesive and smokable material 420 are coated onto the outermost layer of the heating element 410.

In this embodiment, identifiable layers of adhesive 310, 320 are arranged on the support layers 411, 413, which themselves surround the electrically conductive material 412. Portions 421, 422 of the smokable material are layers disposed on top of the adhesive layers 310, 320. In other embodiments, separate layers of adhesive and smokable material 420 cannot be identified. A layer comprising the adhesive and smokable material may be disposed on the support layers 411, 413. The smokable material 420 may be at least partially or completely dispersed within the adhesive.

In some embodiments, the cartridge 40 contains a mass of thermal insulation material between the heating device 400 and the housing 43. By "mass of thermal insulation material", it is meant that the thermal insulation material is not a gas or not merely a gas.

Figure 21:
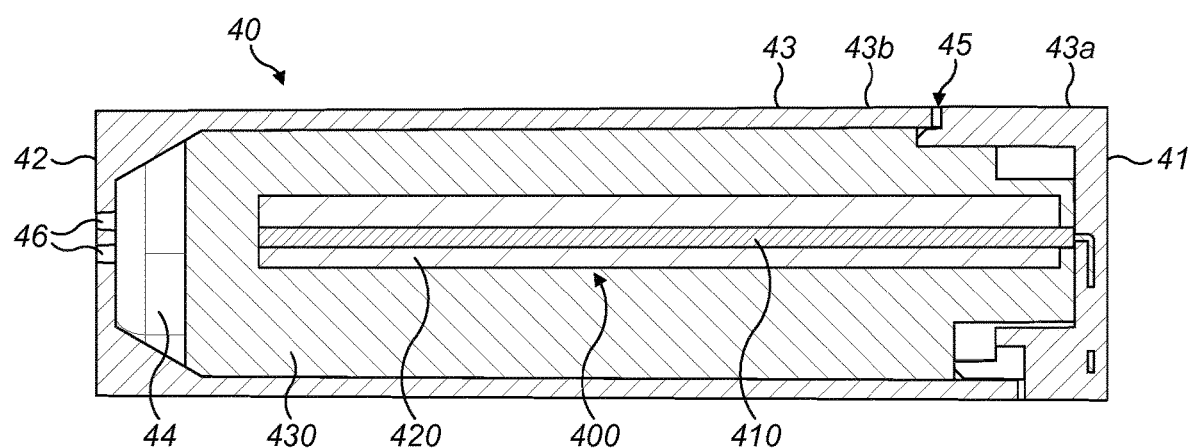
FIG. 21 shows a schematic cross-sectional view of a cartridge.

For example, in the embodiment shown in FIG. 21, the cartridge 40 is the same as the cartridge 40 shown in FIG. 15 except that the cartridge of FIG. 21 includes a mass of thermal insulation material 430 between the heating device 400 and the housing 43. In this embodiment, the thermal insulation material 430 surrounds the heating device 400, fills a space between the heating device 400 and the housing 43, and is in contact with the housing 43 and the smokable material 420 of the heating device 400. In other embodiments, the thermal insulation material 430 may encircle the heating device 400 without fully surrounding the heating device 400. In some embodiments, the thermal insulation material 430 may be in contact with only one of the housing 43 and the heating device 400, and may not fill the space therebetween.

In the embodiment of FIG. 21, the thermal insulation material 430 comprises wadding. However, in other embodiments, the thermal insulation material 430 may comprise one or more materials selected from the group consisting of: wadding, fleece, non-woven material, non-woven fleece, woven material, knitted material, nylon, foam, closed cell foam, polystyrene, closed cell polystyrene foam, polyester, polyester filament, polypropylene, a blend of polyester and polypropylene. Other types of thermal insulation material may also be suitable.

In the cartridge 40 shown in FIG. 21, the thermal insulation material 430 has a density of about 100 grams per square meter (gsm) and a thickness of about 1.2 millimeters. In other embodiments, one or both of the thickness and the density of the thermal insulation material 430 may be different. However, if the density is too high, the thermal insulation material 430 may act as a filter and attenuate the aerosol output from the heating device 400. Alternatively, if the density is too low, the thermal insulation material 430 may not provide effective thermal insulation. An appropriate density, particularly when the thermal insulation material 430 comprises wadding or fleece, may be between about 60 and about 140 gsm, or between about 80 and about 120 gsm.

When the thermal insulation material 430 comprises a material other than wadding or fleece, a density of the thermal insulation material 430 may be chosen to effect similar thermal properties to those achieved when the thermal insulation material 430 comprises wadding or fleece of the above density. In some embodiments, the mass of thermal insulation material 430 is heat resistant at least over the expected range of temperatures of the heating element 410 that will arise in operation, such as for example 180 to 220 degrees Celsius as discussed above, and will not degrade when subjected to such operation temperatures.

In some embodiments, the cartridge 40 comprises thermal insulation material in the form of a laminate or sandwich structure having a plurality of layers of material. In some such embodiments, an outer layer of the layers of material forms the housing 43, or a portion of the housing 43, of the cartridge 40, and one or more other layers of the sandwich structure forms the mass of thermal insulation material 430. Accordingly, in some embodiments, the housing 43, or a portion of the housing 43, may be integrally formed with the mass of thermal insulation material 430.

In some embodiments, the thermal insulation material helps to retard heat loss from the heating device 400 in use. In some embodiments, the thermal insulation material helps to ensure that volatilized material generated in the chamber 44 in use does not condense on the inner surface of the housing 43. In some embodiments, the provision of the mass of thermal insulation material helps to increase the surface area on which aerosol generated in the cartridge 40 in use may form. In some embodiments, a head space remains between the mass of thermal insulation material and the housing 43, which further helps to increase the surface area on which aerosol generated in the cartridge 40 may form in use. In some embodiments, such a mass of thermal insulation material helps to increase the amount of aerosol generated in the cartridge 40 in use, and thus may enhance the consumer experience.

While the cartridge 40 shown in FIG. 21 is a variation of the cartridge 40 shown in FIG. 15, similarly, in respective variations to the embodiments shown in FIGS. 18 to 20, the cartridge 40 may comprise a mass of thermal insulation material between the heating device 400 and the housing 43. Indeed, in respective variations to each of the embodiments of a cartridge 40 discussed herein, the cartridge 40 may comprise a mass of thermal insulation material between the heating device 400, or heating element 410, and the housing 43.

In some embodiments, in which the heating element 410 or the smokable material 420 is omitted from the cartridge 40, the mass of thermal insulation material may be provided in the cartridge 40 between the housing 43 and the smokable material 420 or the heating element 410, respectively. In some such embodiments, the mass of thermal insulation material encircles and/or contacts the smokable material 420 or the heating element 410, respectively. In some such embodiments, the mass of thermal insulation material contacts the housing 43 and/or fills a space between the housing 43 and the smokable material 420 or the heating element 410, respectively.

Generally speaking, the heating device 400 may be manufactured by locating the layer 412 of electrically-conductive material between the first layer 411 of material and the second layer 413 of material to form the heating element 410, and arranging the smokable material 420 on the heating element 410. In this embodiment of the method, the smokable material 420 is arranged on the heating element 410 after the layer 412 of electrically-conductive material has been located between, and in contact with, the first and second support layers, 411, 413.

In this embodiment of the method, the method comprises patterning the electrically-conductive material, such as by etching or printing the electrically-conductive material for example, to form the layer 412 of electrically-conductive material. In some embodiments, the electrically-conductive material is located on one of the first and second support layers 411, 413, then patterned, and then the other of the first and second support layers 411, 413 is applied to locate the layer 412 of electrically-conductive material between the first and second support layers 411, 413. In other embodiments, the electrically-conductive material is patterned and then located between the first and second support layers 411, 413. In some embodiments, the electrically-conductive material may be located between the first and second support layers 411, 413 and then patterned. In still further embodiments, the method does not comprise patterning the electrically-conductive material.

When manufacturing the heating device, the electrically-conductive material of the layer 412 of electrically-conductive material is stainless steel. However, in other embodiments, the electrically-conductive material may be a different metal alloy, or a metal, as discussed above.

In this embodiment of the manufacturing method, each of the first and second layers 411, 413 of material is a layer of polyimide. However, as discussed above, in other embodiments the material of the first support layer 411 may be other than polyimide, and/or the material of the second support layer 413 may be other than polyimide. In some embodiments, the first and second support layers 411, 413 are layers of respective different materials.

In this embodiment of the manufacturing method, the smokable material 420 comprises tobacco and the method comprises bonding the smokable material 420 to the heating element 410. More specifically, and as discussed above, the first portion 421 of the smokable material 420 is bonded to the first support layer 411 and the second portion 422 of the smokable material 420 is bonded to the second support layer 413. As discussed above, in other embodiments, the smokable material 420 may be arranged on the heating element 410 in a number of different ways, such as only on one side of the heating element 410. However, for conciseness, detailed discussion of the various possible arrangements will not be provided again. In this embodiment, the bonding comprises bonding the smokable material 420 by an adhesive to the heating element 410 as described in more detail herein. In some other embodiments, the adhesive may be omitted and the method may comprise bonding the smokable material 420 to the heating element 410 by some other mechanism, or otherwise arranging the smokable material on the heating element 410.

In this embodiment, after the electrically conductive material is located between the support layers 411, 413, the heating element 410 is annealed at 200° C. and surface treated using an oxygen plasma, suitably by corona treatment. The treated heating element is then dipped into an aqueous solution of a polysaccharide (such as hydroxypropyl methyl cellulose or an aqueous solution comprising alginic acid or salt thereof) so as to coat some or all of the support layers 411, 413. The heating element 410 is then removed from the aqueous solution and subsequently dipped into a smokable material so as to coat some or all of the adhesive. The heating element 410 is then removed from the smokable material, and the adhesive hardens or is hardened by curing, drying and/or setting. In other embodiments, the separate adhesive and smokable material layers may be added by sequential spraying steps, or by other methods known to a person skilled in the art; for example, the adhesive may be applied using spray coating, transfer coating, slot die extruding and the smokable material may be added using spray coating, fluidized bed, electrostatic coating. In these embodiments, layers of the adhesive 310, 320 are disposed on the support layers 411, 413. Portions 421, 422 of smokable material 420 are adhered to the support layers 411, 413 by the adhesive layers. The portions 421, 422 of smokable material 420 are arranged substantially separate from the adhesive layers 310, 320.

The solution concentration of the aqueous solution is selected to have a suitable viscosity, having a low enough viscosity that it can easily be applied to the heating element, and a high enough viscosity such that it can be retained on the surface of the heating element before it is hardened. The polysaccharide concentration in an aqueous solution may be from about a 2% w/w, 4% w/w or 5% w/w solution to about a 7% w/w, 8% w/w or 10% w/w solution (suitably a 2-10% w/w solution, or a 5-7% w/w solution).

In other embodiments, the smokable material 420 and adhesive may not be in identifiably separate layers. By way of an example, the smokable material may be initially dispersed in a polysaccharide solution. The heating element 410 may then dipped into this dispersion, or the dispersion may be sprayed onto the heating element 410 to from a single layer on the surface of the support layers 411, 413, the single layer comprising both the adhesive and the smokable material 420.

In this embodiment, and as indicated in FIG. 12, the cartridge 40 comprises two electrically-conductive terminals 47a, 47b, which herein are referred to as a "seventh electrically-conductive terminal" 47a and an "eighth electrically-conductive terminal" 47b, respectively. The heating element 410 is electrically connected across the seventh and eighth electrically-conductive terminals 47a, 47b and is heatable by passing an electric current through the heating element 410 via the seventh and eighth electrically-conductive terminals 47a, 47b. The seventh and eighth electrically-conductive terminals 47a, 47b are located in respective recesses, but are accessible from the exterior of the cartridge 40. In this embodiment, when the cartridge 40 is fully received in the recess 13, the seventh and eighth electrically-conductive terminals 47a, 47b are in surface contact with the first and second electrically-conductive terminals 17b, 17c, respectively. Accordingly, the heating element 410 can be caused to heat by applying electrical power to the first and second electrically-conductive terminals 17b, 17c.

In some embodiments, the cartridge 40 is able to be received fully in the recess 13 in only one orientation relative to the first casing portion 10. In this embodiment, this is due to the cartridge 40, and more specifically the housing 43, having an asymmetric exterior cross-sectional shape that corresponds to an asymmetric interior cross-sectional shape of the recess 13. In other embodiments, the cartridge 40 may be able to be received in the recess 13, or able to co-operate with the interface, in only one orientation relative to the first casing portion 10 due to the provision of one or more other mechanisms. For example, in some embodiments, the housing 43 of the cartridge 40 may have rotational symmetry and thus have a symmetric exterior cross-sectional shape, and the cartridge 40 may have a key projecting from the housing 43 that gives the overall cartridge 40 an asymmetric exterior cross-sectional shape that corresponds to an asymmetric interior cross-sectional shape of the recess 13. Providing that the cartridge 40 is able to co-operate with the interface in only one orientation relative to the first casing portion 10 helps to ensure that the cartridge 40 is correctly assembled with the rest of the apparatus 1 with the seventh and eighth electrically-conductive terminals 47a, 47b in surface contact with the first and second electrically-conductive terminals 17b, 17c, respectively. However, in some embodiments, the cartridge may be receivable fully in the recess 13 in more than one orientation relative to the first casing portion 10.

As discussed above, in this embodiment the controller 50 is for controlling the supply of electrical power to the heating element 410 from the electrical power source 24, when the interface 13 is co-operating with the cartridge 40. When the apparatus 1 is fully assembled with the first connector 15 fully engaged with the second connector 25, and with the cartridge 40 fully and correctly received in the recess 13, actuation of the actuator 18 by a user causes the controller 50 to cause an electric current to be applied across the seventh and eighth electrically-conductive terminals 47a, 47b, and thus across the heating element 410. Such actuation of the actuator 18 may cause completion of an electrical circuit in the controller 50. As the electric current is so applied across the heating element 410, the heating element 410 heats up so as to heat the smokable material 420. In this embodiment, the electrical resistance of the heating element 410 changes as the temperature of the heating element 410 increases. The controller 50 monitors the electrical resistance of the heated heating element 410 and then adjusts the magnitude of the electrical current applied across the heating element 410 on the basis of the monitored electrical resistance as necessary, in order to ensure that the temperature of the heating element 410 remains within the above-discussed temperature range of about 180 degrees Celsius to about 220 degrees Celsius. Within this temperature range, the smokable material 420 is heated sufficiently to volatilize at least one component of the smokable material 420 without combusting the smokable material 420. Accordingly, the controller 50, and the apparatus 1 as a whole, is arranged to heat the smokable material 420 to volatilize the at least one component of the smokable material 420 without combusting the smokable material 420. In other embodiments, the temperature range may be other than this range.

As discussed above, the plate 16 has five holes 16a-16e therethrough, and the first to third pins 17a, 17b, 17c are provided in the first to third 16a, 16b, 16c of these holes. The fourth and fifth holes 16d, 16e of the five holes 16a-16e remain open and fluidly connect the recess 13 with the inlets 60 defined by the cooperation of the first and second connectors 15, 25. Moreover, when the cartridge 40 is fully received in the recess 13, the air flow path 45 defined by the cooperation of the first and second housing parts 43a, 43b of the cartridge 40 is fluidly connected with the recess 13. Accordingly, and as shown in FIG. 16, in the fully-assembled apparatus 1, there is defined an overall flow path that extends from the exterior of the apparatus 1, then through any one of the inlets 60 defined by the cooperation of the first and second connectors 15, 25, then through either one of the fourth and fifth holes 16d, 16e in the plate 16, then through the recess 13, then through the air flow path 45 defined by the cooperation of the first and second housing parts 43a, 43b of the cartridge 40, then through the chamber 44 of the cartridge 40, then through any one of the apertures 46 extending through the housing 43 of the cartridge 40, and then through the channel 36 of the mouthpiece 30 to the exterior of the apparatus 1. The seal 37 of the mouthpiece 30 prevents air from bypassing the chamber 44 of the cartridge 40 when travelling from the recess 13 to the channel 36 of the mouthpiece 30.

An exemplary operation of the apparatus 1 of this embodiment will now be described. A user ensures that the mouthpiece 30 is at a location relative to the first casing portion 10 at which the cartridge 40 is movable through the opening 14. The user then passes the cartridge 40 through the opening 14 and into the recess 13 so as to bring the seventh and eighth electrically-conductive terminals 47a, 47b of the cartridge 40 into surface contact with the first and second electrically-conductive terminals 17b, 17c, respectively. The user then moves the mouthpiece 30 relative to the first casing portion 10 to a location at which the mouthpiece 30 covers the opening 14, with the outlet 35 of the mouthpiece 30 at the exterior of the apparatus 1, and with the seal 37 contacting and compressing against the cartridge 40 and surrounding the apertures 46. The mouthpiece 30 is retained at this location through engagement of the connector 33 of the mouthpiece 30 with the second connector 19 of the first casing portion 10.

Before, during or after such movements of the cartridge 40 and mouthpiece 30 relative to the first casing portion 10, the user also ensures that the first connector 15 of the first casing portion 10 is fully engaged with a second connector 25 of the second casing portion 20. As discussed above, when the first and second connectors 15, 25 are fully engaged, the third electrically-conductive terminal 17a is in surface contact with the fourth electrically-conductive terminal 283a, and the fifth electrically-conductive terminal 15a is in surface contact with the sixth electrically-conductive terminal 25a.

When the actuator 18 is subsequently actuated by actuated by the user, the controller 50 is operated to cause an electric current to be applied across the seventh and eighth electrically-conductive terminals 47a, 47b and thus across the heating element 410. This application of the electric current causes the heating element 410 to heat up so as to heat the smokable material 420 to volatilize at least one component of the smokable material 420 without combusting the smokable material 420, as discussed above. Typically, this volatilization causes the formation of an aerosol in the chamber 44 of the cartridge 40. The user inhales the aerosol by drawing on the outlet 35 of the mouthpiece 30. This causes the aerosol to be drawn from the chamber 44 of the cartridge 40 and into the user's mouth via the apertures 46 of the cartridge 40 and via the channel 36 of the mouthpiece 30. This drawing of the aerosol from the chamber 44 of the cartridge 40 causes a reduction in pressure in the chamber 44. This reduction in pressure causes air to be drawn into the chamber 44 via the annular gap 62, the inlets 60 defined between the first and second connectors 15, 25, the fourth and/or fifth holes 16d, 16e in the plate 16, the recess 13, and the air flow path 45 defined by the cooperation of the first and second housing parts 43a, 43b of the cartridge 40, in turn. The user is able to carry out subsequent such inhalations to inhale subsequent volumes of the aerosol.

When the smokable material 420 has been spent, or substantially all of the smokable material 420 has been spent, the user may move the mouthpiece 30 relative to the first casing portion 10 to a location at which the cartridge 40 is movable through the opening 14. The user may then remove the cartridge 40 from the recess 13 via the opening 14. The user can subsequently insert another, unspent cartridge 40 into the recess 13 and repeat the above process. The heating element 410 may become dirtied with the volatilized material or the spent smokable material 420 in use. By locating the heating element 410 in the cartridge 40, rather than in the first casing portion 10, each time a new, unspent cartridge 40 is used, the user is provided with a fresh heating element 410. Accordingly, the user does not need to be concerned with cleaning the heating element 410.

In some embodiments, the apparatus 1 is provided fully assembled. In the fully assembled state, the first connector 15 of the first casing portion 10 is engaged with the second connector 25 of the second casing portion 20, and the connector 33 of the mouthpiece is engaged with the second connector 19 of the first casing portion 10. In some such embodiments, the cartridge 40 is located in the recess 13. In other such embodiments, no cartridge 40 is in the recess 13. In other embodiments, the apparatus 1 may be in kit form, with the first connector 15 of the first casing portion 10 disengaged from, but engageable with, the second connector 25 of the second casing portion 20 and/or with the connector 33 of the mouthpiece disengaged from, but engageable with, the second connector 19 of the first casing portion 10. In some such kit-form apparatuses, the cartridge 40 may be located in the recess 13. In other such kit-form apparatuses, one or more examples of the cartridge 40 may be provided as part of the apparatus but outside of the recess 13.

In this embodiment, the apparatus 1 has only one heating element. In other embodiments, the apparatus 1 may have more than one heating element. In this embodiment, the cartridge 40 is intended to be used and then replaced by an alternative cartridge 40, as discussed above. However, in other embodiments, the cartridge 40 may not be replaceable and the apparatus 1 may be for only single use. In some embodiments, the apparatus 1 may not include a cartridge 40. In some embodiments, the heating element 410, or the heating device 400, may be integral with the first casing portion 10 and may be irremovable from the first casing portion 10. In some embodiments, the electrical power source 24 may be integral with the second casing portion 20 and may be irremovable from the second casing portion 20. In some embodiments, the first casing portion 10 may be integral or unitary with the second casing portion 20, or may be permanently fixed to the second casing portion 20. Therefore, in some embodiments, the casing of the apparatus 1 may be a one-piece casing, and may not have the first and second connectors 15, 25 discussed above. In some embodiments, the positive and negative terminals 24a, 24b of the electrical power source 24 may be permanently electrically connected to the controller 50. In some embodiments, the mouthpiece 30 may be immovable relative to the first casing portion 10. In some embodiments, the mouthpiece 30 may be integral or unitary with the first casing portion 10.

In each of the embodiments discussed above, the smokable material 420 is arranged on a support that is a heating element 410. However, in some embodiments, the support may be other than a heating element 410. In some embodiments in which the support is other than a heating element 410, the support may have any of the features of the heating element 410 discussed herein. In some embodiments in which the support is other than a heating element 410, the smokable material 420 may have any of the features of the smokable material 420 discussed herein, and so may be arranged on the support in any of the manners discussed herein for the arrangement of the smokable material 420 on the heating element 410. In some embodiments in which the support is other than a heating element 410, the smokable material 420 and the support may be comprised in a device, rather than a heating device as such.

In order to address various issues and advance the art, the entirety of this disclosure shows by way of illustration and example various embodiments in which the claimed invention may be practiced and which provide for a superior apparatus for heating smokable material to volatilize at least one component of the smokable material. The advantages and features of the disclosure are of a representative sample of embodiments only, and are not exhaustive and/or exclusive. They are presented only to assist in understanding and teach the claimed and otherwise disclosed features. It is to be understood that advantages, embodiments, examples, functions, features, structures and/or other aspects of the disclosure are not to be considered limitations on the disclosure as defined by the claims or limitations on equivalents to the claims, and that other embodiments may be utilized and modifications may be made without departing from the scope and/or spirit of the disclosure. Various embodiments may suitably comprise, consist of, or consist in essence of, various combinations of the disclosed elements, components, features, parts, steps, means, etc. The disclosure may include other inventions not presently claimed, but which may be claimed in future.

The invention claimed is:

1. A cartridge for use with an apparatus for heating a smokable material to volatilize at least one component of the smokable material, the cartridge comprising:
    a housing defining a chamber;
    a heating element located in the chamber, wherein the heating element is heated by electric current within the heating element and receives power from an electrical power source that is located within the apparatus for heating the smokable material and external of the cartridge;
    the smokable material being in a solid state or in the form of a gel, the smokable material bonded to the heating element and located in the chamber; and
    a mass of thermal insulation material located between the smokable material and the housing,
    wherein the cartridge is configured to releasably engage with the apparatus, and wherein the heating element is inaccessible to a user.

2. The cartridge according to claim 1, wherein the thermal insulation material encircles the smokable material.

3. The cartridge according to claim 1, wherein the thermal insulation material is in contact with the smokable material.

4. The cartridge according to claim 1, wherein the thermal insulation material fills a space between the smokable material and the housing.

5. The cartridge according to claim 1, wherein the smokable material comprises tobacco.

6. The cartridge according to claim 1, wherein the smokable material is in a solid state.

7. The cartridge according to claim 1, wherein the smokable material is bonded to at least two sides of the heating element.

8. The cartridge according to claim 1, wherein the thermal insulation material is in contact with the housing.

9. The cartridge according to claim 1, wherein the thermal insulation material comprises one or more materials selected from the group consisting of: wadding, fleece, non-woven material, non-woven fleece, woven material, knitted material, nylon, foam, closed cell foam, polystyrene, closed cell polystyrene foam, polyester, polyester filament, polypropylene, and a blend of polyester and polypropylene.

10. The cartridge according to claim 1, wherein the thermal insulation material has a density of from about 60 to about 140 gsm.

11. The cartridge according to claim 1, wherein the cartridge has an asymmetric exterior cross-sectional shape.

12. The cartridge according to claim 1, further comprising two electrically-conductive terminals that are accessible from an exterior of the cartridge, wherein the heating element is electrically connected across the electrically-conductive terminals.

13. The cartridge according to claim 1, wherein the thermal insulation material is configured to prevent volatilized material generated in the chamber from condensing on an inner surface of the housing.

14. A cartridge for use with an apparatus for heating a smokable material to volatilize at least one component of the smokable material, the cartridge comprising:
    a housing defining a chamber;
    a heating element located in the chamber, wherein the heating element is heated by electric current within the heating element and receives power from an electrical power source that is located within the apparatus for heating the smokable material and external of the cartridge; and
    a mass of thermal insulation material located between the heating element and the housing,
    wherein the cartridge is configured to releasably engage with the apparatus, wherein the heating element is inaccessible to a user, and wherein the smokable material is in a solid state or in the form of a gel, and the smokable material bonded to the heating element.

15. The cartridge according to claim 14, wherein the thermal insulation material encircles the heating element.

16. The cartridge according to claim 14, further comprising two electrically-conductive terminals that are accessible from an exterior of the cartridge, wherein the heating element is electrically connected across the electrically-conductive terminals.

17. The cartridge according to claim 14, wherein the thermal insulation material being located between the smokable material and the housing.

18. The cartridge according to claim 17, wherein the thermal insulation material is in contact with the smokable material.

19. The cartridge according to claim 17, wherein the thermal insulation material fills a space between the smokable material and the housing.

20. The cartridge according to claim 14, wherein the thermal insulation material is configured to prevent volatilized material generated in the chamber from condensing on an inner surface of the housing.

21. The cartridge according to claim 14, wherein the thermal insulation material has a density of from about 60 to about 140 gsm.

22. An apparatus for heating a smokable material to volatilize at least one component of the smokable material, the apparatus comprising:
    an assembly having an interface; and
    a cartridge comprising:
        a housing defining a chamber;
        a heating element located in the chamber, wherein the heating element is heated by electric current within the heating element and receives power from an electrical power source, which is located within the assembly;
        the smokable material being in a solid state or in the form of a gel, the smokable material bonded to the heating element and located in the chamber; and
        a mass of thermal insulation material located between the smokable material and the housing, wherein the cartridge is for releaseably co-operating with the interface of the assembly, and wherein the heating element is inaccessible to a user.

23. The apparatus according to claim 22, wherein the assembly comprises a controller arranged to control heating of the heating element so as to cause heating of the smokable material to volatilize the at least one component of the smokable material without combusting the smokable material when the cartridge is co-operating with the interface of the assembly.

* * * * *